US005777194A

United States Patent [19]
Scott et al.

[11] Patent Number: 5,777,194
[45] Date of Patent: Jul. 7, 1998

[54] GENE-TARGETED MICE WITH HUMANIZED Aβ SEQUENCE AND SWEDISH FAD MUTATION

[75] Inventors: Richard W. Scott, Wallingford; Andrew G. Reaume, West Chester; Stephen P. Trusko, Avondale, all of Pa.; Robert Siman, Wilmington, Del.

[73] Assignee: Cephalon, Inc., West Chester, Pa.

[21] Appl. No.: 636,876

[22] Filed: Apr. 23, 1996

Related U.S. Application Data

[63] Continuation-in-part of Ser. No. 429,207, Apr. 26, 1995, abandoned.

[51] Int. Cl.$^6$ .............................. C12N 5/00; C12N 15/00; A61K 49/00
[52] U.S. Cl. ..................... 800/2; 800/DIG. 1; 424/9.2; 935/63
[58] Field of Search ................................. 800/2, DIG. 1; 424/9.1, 9.2; 935/63

[56] References Cited

U.S. PATENT DOCUMENTS 5,387,742   2/1995   Cordell.

FOREIGN PATENT DOCUMENTS

| | | |
|---|---|---|
| 0 653 154 | 5/1995 | European Pat. Off.. |
| WO 93/14200 | 7/1993 | WIPO. |
| WO 94/12627 | 6/1994 | WIPO. |
| WO 95/11968 | 5/1995 | WIPO. |
| WO 95/20666 | 8/1995 | WIPO. |

OTHER PUBLICATIONS

Breen et al., "Beta Amyloid Precursor Protein Mediates Neuronal Cell–Cell and Cell–Surface Adhesion," *J. of Neurosci. Res.*, (1991) 28:90–100.

Bush et al., "Rapid Induction of Alzheimer Aβ Amyloid Formation by Zinc," *Science* (1994) 265:1464–67.

Buxbaum et al., "Expression of APP in Brains of Transgenic Mice Containing the Entire Human APP Gene," *Biochemical and Biophysical Research Communications* (1993) 197:639–45.

Cai et al., "Release of Excess Amyloid β Protein from a Mutant Amyloid β Protein Precursor," *Science* (1993) 259:514–516.

Citron et al., "Excessive Production of Amyloid β–Protein by Peripheral Cells of Symptomatic and Presymptomatic Patients Carrying the Swedish Familial Alzheimer Disease Mutation," *Proc. Natl. Acad. Sci. USA* (1994) 91:11993–11997.

Citron et al., "Generation of Amyloid β Protein from Its Precursor is Sequence Specific," *Neuron* (1995) 14:661–670.

Citron et al., "Mutation of the β–Amyloid Precursor Protein in Familial Alzheimer's Disease Increases β–Protein Production," *Nature* (1992) 360:672–674.

Crawford et al., "Alzheimer's Disease Untangled," *BioEssays* (1992) 14:727–734.

Estus et al., "Potentially Amyloidogenic, Carboxyl–Terminal Derivatives of the Amyloid Protein Precursor," *Science* (1992) 255:726–728.

Games et al., "Alzheimer–type Neuropathology in Transgenic Mice Overexpressing V717F β–Amyloid Precursor Protein," *Nature* (1995) 373:523–527.

Goldgaber et al., "Characterization and Chromosomal Localization of a cDNA Encoding Brain Amyloid of Alzheimer's Disease," *Science* (1987) 235:877–880.

Higgins et al., "Transgenic Mice Expressing Human β–APP751, But Not Mice Expressing β–APP695, Display Early Alzheimer's Disease–like Histopathology," *Annals New York Academy of Sciences* 695:224–227.

Kammesheidt et al., "Deposition of β/A4 Immunoreactivity and Neuronal Pathology in Transgenic Mice Expressing the Carboxyl–terminal Fragment of the Alzheimer Amyloid Precursor in the Brain," *Proc. Natl. Acad. Sci. USA*, (1992) 89:10857–10861.

Kang et al., "The precursor of Alzheimer's disease amyloid A4 protein resembles a cell–surface receptor," *Nature*, (1987) 325:733–736.

Kim et al., "Detection and Quantitation of Amyloid β–Peptide with 2 Monoclonal Antibodies," *Neuroscience Research Communications*, (1990) 7:113–122.

Lamb et al., "Introduction and Expression of the 400 Kilobase Precursor Amyloid Protein Gene in Transgenic Mice," *Nature Genetics* (1993) 5:22–30.

McConlogue et al., "Transgenic Mice Expressing Human Alzheimer's β–Amyloid Precursor Protein Produce High Amounts of β–Peptide," Fourth International Conference on Alzheimer's Disease, p. S12 (Abstract No. 49).

Mattson et al., "Evidence for Excitoprotective and Intraneuronal Calcium–Regulating Roles for Secreted Forms of the β–Amyloid Precursor Protein," *Neuron* (1993) 10:243–254.

Mucke et al., "Synaptotrophic Effects of Human Amyloid β Protein Precursors in the Cortex of Transgenic Mice," *Brain Research* (1994) 666:151–167.

Mullan et al., "A Pathogenic Mutation for Probable Alzheimer's Disease in the APP Gene at the N–terminus of β–Amyloid," *Nature Genetics* (1992) 1:345–347.

Muller et al., "Behavioral and Anatomical Deficits in Mice Homozygous for a Modified β–Amyloid Precursor Protein Gene," *Cell* (1994) 79:755–765.

Oltersdorf et al., "The Secreted Form of the Alzheimer's Amyloid Precursor Protein with the Kunitz Domain is Protease Nexin–II," *Nature* (1989) 341:144–147.

Otvos et al., "Human and Rodent Alzheimer β–Amyloid Peptides Acquire Distinct Conformations in Membrane–Mimicking Solvents," *European J. Biochem.* (1993) –:249–257.

(List continued on next page.)

*Primary Examiner*—Deborah Crouch
*Attorney, Agent, or Firm*—Fish & Richardson P.C.

[57] ABSTRACT

Disclosed is non-human mouse homozygous for a targeted amyloid precursor protein-encoding gene comprising: (1) a human Aβ peptide-encoding sequence in place of the native Aβ peptide-encoding sequence; and (2) Swedish FAD mutations.

5 Claims, 24 Drawing Sheets

OTHER PUBLICATIONS

Pearson et al., "Expression of the Human β-Amyloid Precursor Protein Gene From a Yeast Artificial Chromosome in Transgenic Mice," *Proc. Natl. Acad. Sci. USA* (1993) 90:10578–10582.

Quon et al., "Formation of β-Amyloid Protein Deposits in Brains of Transgenic Mice," *Nature* (1991) 352:239–241.

Robakis et al., "Molecular Cloning and Characterization of a cDNA Encoding the Cerebrovascular and the Neuritic Plaque Amyloid Peptides," *Proc. Natl. Acad. Sci. USA* (1987) 84:4190–4194.

Saitoh et al., "Secreted Form of Amyloid β Protein Precursor Is Involved in the Growth Regulation of Fibroblasts," *Cell* (1989) 58:615–622.

Sandhu et al., "Expression of the Human β-Amyloid Protein of Alzheimer's Disease Specifically in the Brains of Transgenic Mice," *The Journal of Biological Chemistry* (1991) 266:21331–21334.

Tanzi et al., "Protease Inhibitor Domain Encoded by an Amyloid Protein Precursor mRNA Associated with Alzheimer's Disease," *Nature* (1988) 331:528–532.

Van Nostrand et al., "The Predominant Form of the Amyloid β-Protein Precursor in Human Brain is Protease Nexin 2," *Proc. Natl. Acad. Sci. USA* (1991) 88:10302–10306.

Weidemann et al., "Identification, Biogenesis, and Localization of Precursors of Alzheimer's Disease A4 Amyloid Protein," *Cell* (1989) 57:115–126.

Wisniewski et al., "Comparison of Four Staining Methods on the Detection of Neuritic Plaques," *Acta Neuropathol* (1989) 78:22–27.

Yamada et al., "Complementary DNA for the Mouse Homolog of the Human Amyloid Beta Protein Precursor," *Biochemical and Biophysical Research Communications* (1987) 149:665–671.

Yoshikai et al., "Genomic Organization of the Human Amyloid Beta–Protein Precursor Gene," *Gene* (1990) 87:257–263.

Stamler, "A Radical Vascular Connection," *Nature*, 380:108–111 (1996).

Thomas et al., "Beta–amyloid–mediated vasoactivity and vascular endothelial damage," *Nature*, 380:168–171 (1996).

Lannfelt et al (1993) Behav. Brain Res. 57, p. 210, col. 1, parag. 5; & col. 2, parag. 4, lines 8–16.

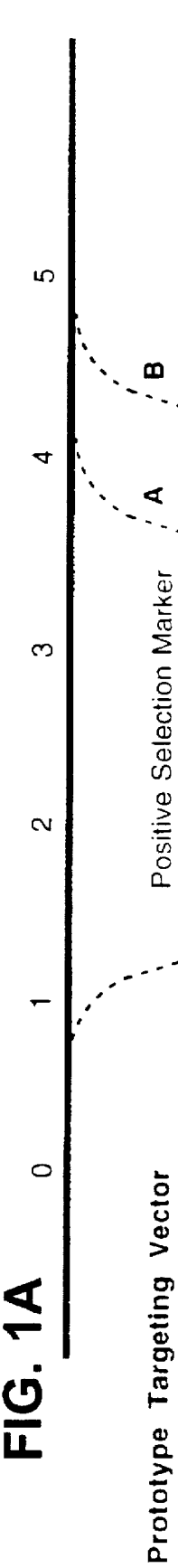
FIG. 1A Gene of Interest
FIG. 1B Prototype Targeting Vector
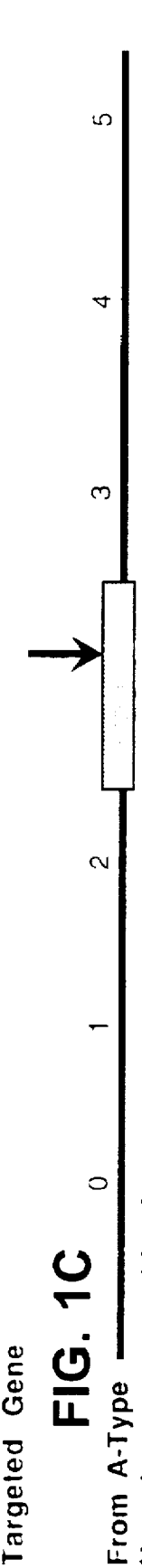
FIG. 1C Targeted Gene
From A-Type Homologous recombination
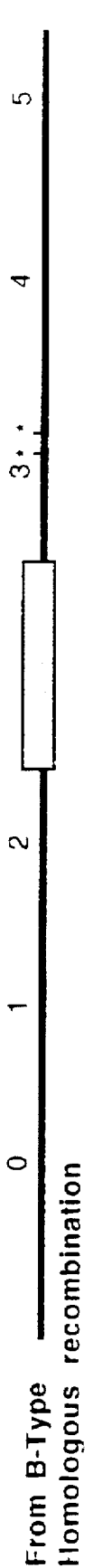
From B-Type Homologous recombination

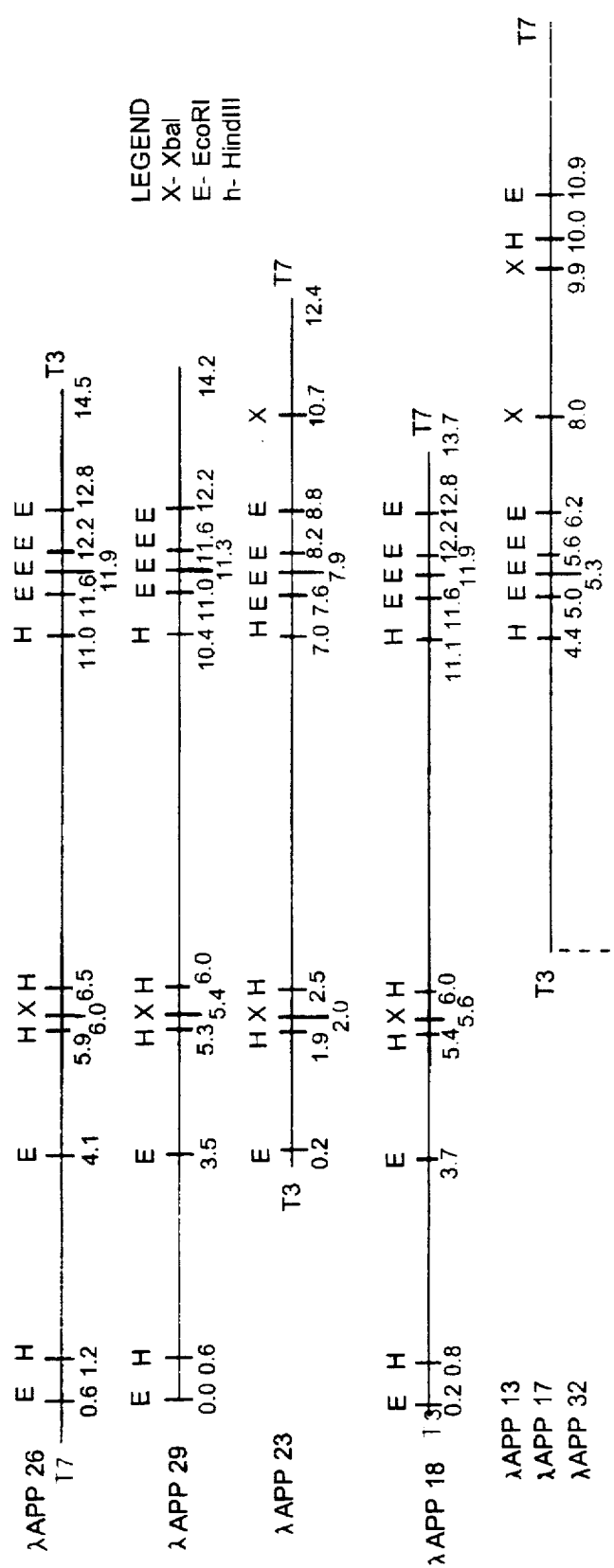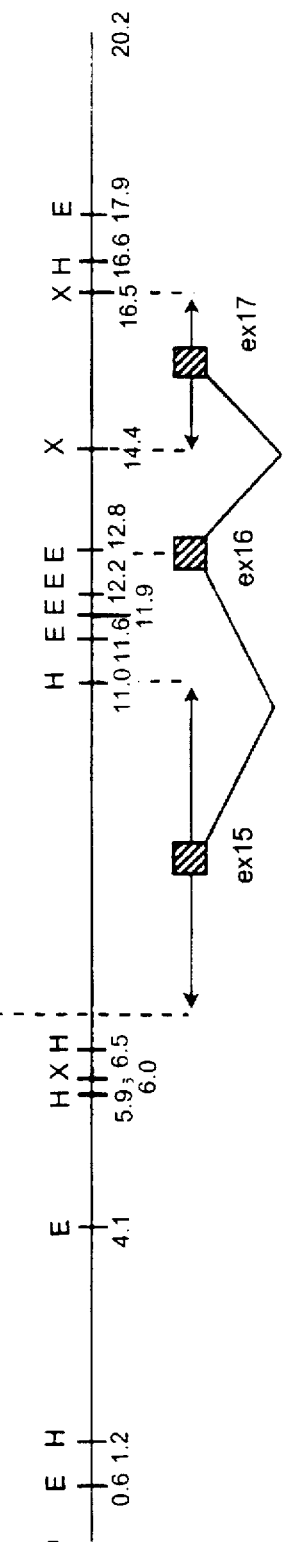
FIG. 2A
FIG. 2B

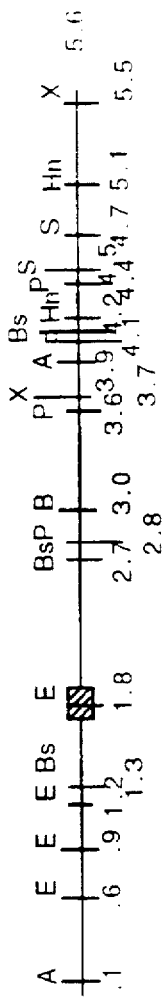
FIG. 10

Detection of Humanized Aβ Epitopes from Targeted ES Cells

Ab 6E10

Ab 4G8

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

ATTGGATCCT TGAGCCTGTT GATGCCCGC     29

( 2 ) INFORMATION FOR SEQ ID NO:2:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

ATTAAGCTTC TCCACCACAC CATGATGAAT     30

( 2 ) INFORMATION FOR SEQ ID NO:3:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

-continued ( x i ) SEQUENCE DESCRIPTION: SEQ ID NO:3:

ATTGGATCCG TTCTGGGCTG ACAAACA 27

( 2 ) INFORMATION FOR SEQ ID NO:4:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

ATTAAGCCTC AGTTTTTGAT GGCGGAC 27

( 2 ) INFORMATION FOR SEQ ID NO:5:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

ATTGGATCCT CGAGCCTGTT GACGCCCG 28

( 2 ) INFORMATION FOR SEQ ID NO:6:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

ATTAAGCCTC TGGTCGAGTG GTCAGAG 27

( 2 ) INFORMATION FOR SEQ ID NO:7:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

ATTGGATCCG TGTTCTTTGC TGAAGAT 27

( 2 ) INFORMATION FOR SEQ ID NO:8:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

ATTAAGCCTC TCCACCACGC CATGATG 27

( 2 ) INFORMATION FOR SEQ ID NO:9:

( i ) SEQUENCE CHARACTERISTICS:
    ( A ) LENGTH: 48 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:9:

GGAAAGAATG CGGCCGCTGT CGACGTTAAC ATGCATATAA CTTCGTAT       48

( 2 ) INFORMATION FOR SEQ ID NO:10:

( i ) SEQUENCE CHARACTERISTICS:
    ( A ) LENGTH: 47 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:10:

GCTCTCGAGA TAACTTCGTA TAGCATACAT TATACGAAGT TATATGC        47

( 2 ) INFORMATION FOR SEQ ID NO:11:

( i ) SEQUENCE CHARACTERISTICS:
    ( A ) LENGTH: 33 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:11:

CGTTCTAGAA TAACTTCGTA TAATGTATGC TAT       33

( 2 ) INFORMATION FOR SEQ ID NO:12:

( i ) SEQUENCE CHARACTERISTICS:
    ( A ) LENGTH: 33 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:12:

CGTGGATCCA TAACTTCGTA TAGCATACAT TAT       33

( 2 ) INFORMATION FOR SEQ ID NO:13:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:13:

AATTCTGCAT CTAGATTCAC TTCCGAGATC TCTTCC       36

( 2 ) INFORMATION FOR SEQ ID NO:14:

( i ) SEQUENCE CHARACTERISTICS:
    ( A ) LENGTH: 39 base pairs

```
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

TGCTCTAGAT GCAGAATTCA GACATGATTC AGGATTTGA                                                    39

( 2 ) INFORMATION FOR SEQ ID NO:15:

( i ) SEQUENCE CHARACTERISTICS:
        ( A ) LENGTH: 58 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

GAATCTAGAT GCAGAATTCA GACATGATTC AGGATATGAA GTCCACCATC AAAAACTG                               58

( 2 ) INFORMATION FOR SEQ ID NO:16:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:16:

CAATCTCGGG GAGAGGCAGT                                                                         20
```

GENE-TARGETED MICE WITH HUMANIZED Aβ SEQUENCE AND SWEDISH FAD MUTATION

This application is a continuation-in-part of U.S. Ser. No. 08/429,207, filed Apr. 26, 1995 now abandoned.

FIELD OF THE INVENTION

This invention relates to gene-targeted non-human mammals and to animal models for human diseases.

BACKGROUND OF THE INVENTION

Alzheimer's Disease (AD) is a human disease for which there is currently no effective treatment. AD is characterized by progressive impairments in memory, behavior, language, and visuo-spatial skills, typically progressing in severity over a 6 to 20-year period, ending in death.

The neocortex, amygdala and hippocampus of the brain are the primary sites of neuropathology in AD. The typical neuropathology of AD comprises extracellular neuritic plaques, intracellular neurofibrillary tangles, neuronal cell loss, gliosis and cerebral vessel amyloid deposition. The neuritic plaques consist of cores of amyloid protein fibrils surrounded by a rim of dystrophic neurites; the plaques have been suggested as the primary site of damage to the cortex. The major protein component of the amyloid protein of the plaque is known as the Aβ peptide, a 4 kD peptide comprising between 39 and 43 amino acids. The Aβ peptide that predominates in plaques has 40 or 42 amino acids.

The Aβ peptide is proteolytically derived from an integral membrane protein known as the β-amyloid precursor protein ("APP"). There are several APP isoforms (having 695, 751 or 770 amino acids), which are encoded by mRNA species resulting from alternative splicing of a common precursor RNA. The APP gene is encoded by a single copy gene found on human chromosome 21 (Estus et al., Science 255:726–728 (1992). The APP gene product ("APP") is alternatively processed via two cellular pathways. Processing in the "amyloidogenic" pathway yields APP fragments bearing the Aβ peptide or the Aβ peptide itself. Alternatively, in the "nonamyloidogenic" pathway, APP is cleaved within the Aβ sequence. This results in destruction of the Aβ peptide and secretion of the large N-terminal ectodomain of APP. The Aβ peptide is produced and secreted by a wide variety of cell types in various animal species. It has been found in body fluids, including serum and cerebral spinal fluid.

Complementary DNAs encoding human APP, have been cloned and sequenced. See, e.g., Kang et al., Nature 325: 733–736 (1987); Goldgaber et al., Science 235:877–880 (1987); Tanzi et al., Nature 331:528–530 (1988); and Robakis et al., Proc. Natl. Acad.Sci. USA 84:4190–4194 (1987). The CDNA for a mouse homolog of human APP has also been cloned and sequenced. Human and murine APP amino acid sequences have a high degree of homology (96.8%), indicating that the protein is conserved across mammalian species (Yamada et al., Biochem. Biophys. Res. Commun. 149: 665–671 (1987)). The mouse Aβ and human Aβ sequences differ at positions 5, 10 and 13 (i.e., positions 676, 681 and 684 of the complete APP770 sequence). The amino acid changes, from mouse to human Aβ, are: Gly to Arg (Aβ 5, APP 676); Phe to Tyr (Aβ10, APP 681); and Arg to His (Aβ 13, APP 684).

A form of Alzheimer's disease known as "Swedish Familial Alzheimer's Disease" has been associated with two mutations known as the "Swedish FAD mutations." The Swedish FAD mutations are transversions (G to T and A to C) in codons 670 and 671 (APP 770 transcript), which are in exon 16 of the APP gene (Mullan, Nature Genetics 1:345–347 (1992)). The Swedish FAD mutations change lysine to asparagine and methionine to leucine at positions 670 and 671, respectively, in the amyloid precursor protein. These amino acid changes are immediately adjacent to the amino terminus of the Aβ peptide.

The Swedish FAD mutations may act by altering the proteolytic processing of APP so that increased amounts of Aβ are released (Cai et al., Science 259:514–516 (1993)). In vitro studies have demonstrated that cells expressing APP with the Swedish FAD mutation produce 3 to 7-fold more Aβ than cells expressing APP without the mutation.

Furthermore, it was shown that the methionine to leucine mutation at amino acid 671 (M671L) is principally responsible for the increase in Aβ production (Citron et al., Nature, 360: 672–674 (1992)). A mutagenesis study to examine substrate requirements of proteases that cleave APP at the amino-terminus of Aβ in human cells grown in tissue culture showed that most amino acid substitutions at position 671 strongly inhibit Aβ production. Except the methionine-to-leucine substitution, the only substitutions at position 671 that did not decrease Aβ production were changes to tyrosine and phenylalanine, both of which are large and hydrophobic residues. Another amino acid that shares these characteristics (but was not tested) is tryptophan. A small number of substitutions at position 670 had no effect on Aβ levels (Citron et al., Neuron 14: 661–670 (1995)).

Genetically engineered non-human mammals may serve as models for at least some aspects of AD. The genetic engineering of non-human mammals (or any other organism) may be carried out according to at least two fundamentally different approaches: (1) random insertion of an exogenous gene into a host organism, and (2) gene targeting. The term "transgenic" has sometimes been used in a broad sense, to indicate any organism into which an exogenous piece of DNA has been incorporated. As used herein, however, the term "transgenic" is reserved for organisms (i.e., non-human mammals) comprising a piece of exogenous DNA that has been randomly inserted. A transgenic organism expresses the transgene in addition to all normally-expressed native genes (except the gene or genes in which the random insertion(s) may have taken place).

Transgenic non-human mammals comprising human APP DNA sequences, in addition to the native APP DNA sequences, are known. See, e.g., Quon et al., (Nature 352: 239–241 (1991)); Higgins et al., (Annals NY Acad Sci. 695:224–227 (1994); Sandhu et al.,(J. Biol. Chem. 266:21331–21334 (1991); Kammesheid et al., (Proc. Natl. Acad. Sci. USA 89:10857–10861 (1992); Lamb et al., (Nature Genet. 5:22–30 (1993); Pearson et al., (Proc. Natl. Acad. Sci. USA 90:10578–10582 (1993); McConlogue et al., (McConlogue et al., Neurobiol. Aging 15, s12 (1994); Games et al., (Nature 373:523–527 (1995); and U.S. Pat. No. 5,387,742.

In contrast, a gene-targeted organism has had a selected native DNA sequence or gene (i.e., targeted gene) partially or completely removed or replaced through a process known as homologous recombination. If the targeted gene is a single-copy gene and the organism is homozygous at that locus, the gene-targeted organism can no longer express the targeted native gene. The organism may or may not express a modified version of the targeted gene, depending on whether the targeted gene was mutated into a modified, but functional form, or mutated into a null allele, i.e., "knocked out." An attempt to produce, by gene targeting, mice homozygous for an APP null allele (and thus devoid of APP), has been published (Muller et al., *Cell* 79:755–765 (1994)). This attempt, wherein exon 2 of the APP gene was disrupted, resulted in mice expressing a shortened form of APP, at 5 to 10-fold lower levels than the expression of normal APP in wild type mice.

SUMMARY OF THE INVENTION

We have discovered that when a humanized APP-encoding gene, comprising the human Aβ peptide encoding sequence and the Swedish FAD mutations, is expressed in a gene-targeted non-human mammal, the human Aβ peptide is produced in the non-human mammal's brain. In non-human mammals homozygous for the targeted APP gene, the human Aβ peptide is produced in the absence of native Aβ peptide. In non-human mammals heterozygous for the targeted APP gene, the human Aβ is produced in the presence of reduced levels of native Aβ peptide (with the reduced level of native Aβ peptide being approximately 50% of that normally produced in wild-type control animals). We have also discovered that when a humanized APP gene, comprising the human Aβ peptide encoding sequence and the Swedish FAD mutations, is expressed in the brain of a gene-targeted non-human mammal, amyloidogenic cleavage at the β-secretase site of APP is enhanced. As a result of this enhanced cleavage, we expect enhanced production of the human Aβ peptide in the brains of the gene-targeted non-human mammals, as compared to production of the native Aβ peptide in the brains of wild-type control animals. In non-human mammals homozygous for the targeted APP gene, the amount of human Aβ peptide produced is approximately twice the amount of human Aβ peptide produced in non-human mammals heterozygous for the targeted APP gene.

Accordingly, in one embodiment, this invention features a non-human mammal homozygous for a targeted APP gene comprising: (1) a human Aβ peptide-encoding sequence in place of the native Aβ peptide-encoding sequence; and (2) at least one Swedish FAD mutation. In another embodiment, the invention features a non-human mammal heterozygous for a targeted APP gene comprising: (1) a human Aβ peptide-encoding sequence in place of the native Aβ peptide-encoding sequence; and (2) at least one Swedish FAD mutation.

The non-human mammals of this invention may be used as tools or models to elucidate the role of human Aβ in AD pathology and symptomatology. The non-human mammals of this invention also may be used as assay systems to screen for in vivo inhibitors of amyloidogenic processing of APP in the non-human mammal's brain, non-brain tissues, or body fluids. Accordingly, the invention features a method for screening chemical compounds for their ability to inhibit in vivo processing of APP to yield the human Aβ peptide in the brain, in non-brain tissues, or in body fluids (e.g., blood and cerebral spinal fluid), said method comprising the steps of: (a) administering said chemical compounds to a non-human mammal homozygous or heterozygous for a targeted APP gene comprising: (1) a human Aβ peptide-encoding sequence in place of the native Aβ peptide-encoding sequence; and (2) Swedish FAD mutations; and (b) measuring the relative amounts of amyloidogenic and nonamyloidogenic processing of amyloid precursor protein in brain tissue, non-brain tissue, or body fluids (or some combination thereof) of said non-human mammal, at an appropriate interval after administration of said chemical compounds.

As used herein, "APP" means amyloid precursor protein.

As used herein, "APP770" means the APP isoform that has 770 amino acid residues. The positions of the amino acid residues in the APP are numbered from 1 to 770, starting at the amino terminus.

As used herein, "arms of homology" means nucleotide DNA sequences in a targeting vector: (1) which have sufficient length and homology to provide for site-specific integration of part of the targeting vector into the target gene by homologous recombination; (2) in which, or between which are located one or more mutations to be introduced into a target gene; and (3) which flank a positive selectable marker.

As used herein, "gene-targeted non-human mammal" means a non-human mammal comprising one or more targeted genes.

As used herein, "homologous recombination" means rearrangement of DNA segments, at a sequence-specific site (or sites), within or between DNA molecules, through base-pairing mechanisms.

As used herein, "humanized APP" means a non-human mammalian APP in which the native Aβ peptide sequence of the APP has been replaced with the human Aβ peptide sequence, and the remainder of the APP molecule, i.e., everything except the Aβ peptide sequence, is unchanged. An APP is said to be "humanized because it consists of a combination of human and native sequences.

As used herein, "human Aβ peptide" means a peptide having the amino acid sequence of the human Aβ peptide, regardless of whether the peptide is proteolytically derived from a human APP or a humanized APP. An Aβ peptide is said to be human, as opposed to humanized, because it consists exclusively of a human sequence.

As used herein, "Swedish FAD mutations" means transversions (G to T and A to C) in codons 670 and 671 (APP 770 transcript), which are in exon 16 of the APP gene. The Swedish FAD mutations change lysine to asparagine and methionine to leucine at positions 670 and 671, respectively, in the amyloid precursor protein.

As used herein, "target gene" means a gene in a cell, which gene is to be modified by homologous recombination with a targeting vector.

As used herein, "targeted gene" means a gene in a cell, which gene has been modified by homologous recombination with a targeting vector.

As used herein, "targeting vector" means a DNA molecule that includes arms of homology, the nucleotide sequence (located within or between the arms of homology) to be incorporated into the target gene, and one or more selectable markers.

As used herein, "wild-type control animal" means a non-gene-targeted, non-human mammal of the same species as, and otherwise comparable to (e.g., similar age), a gene-targeted non-human mammal. A wild-type control animal is the basis for comparison, in assessing results associated with a particular genotype.

Other features and advantages of the invention will be apparent from the following description of the preferred embodiments thereof, and from the claims.

BRIEF DESCRIPTION OF THE FIGURES

FIG. 1 is a schematic diagram illustrating general principles of gene targeting.

FIG. 2 is a set of mouse APP genomic clone maps. Single letter abbreviations for restriction endonucleases are as follows: E, EcoRI; H, HindIII; X, XbaI

FIG. 10 is a pair of restriction maps for the APP 3' and 5' arms of homology.

DETAILED DESCRIPTION

Figure 3:
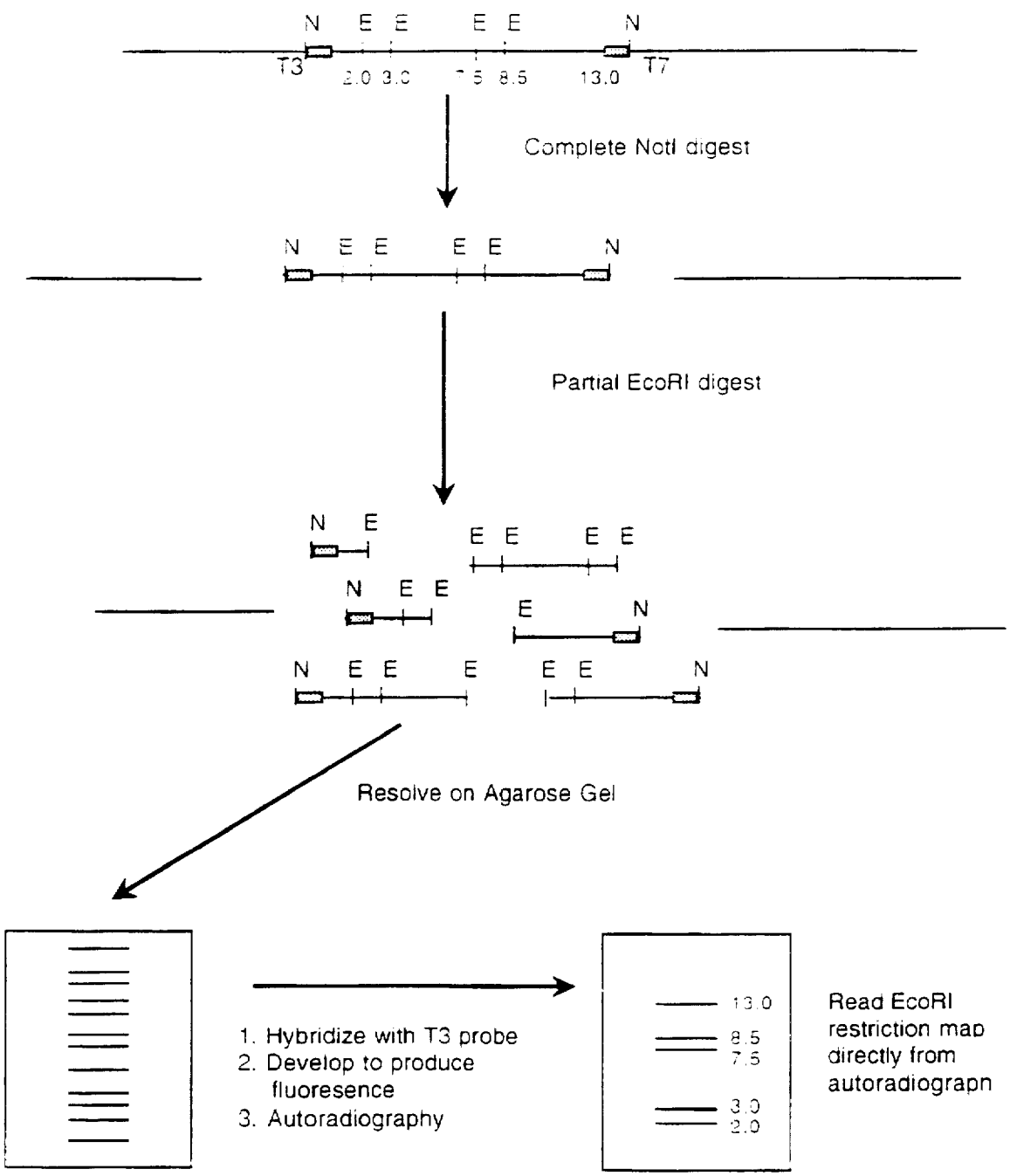
FIG. 3 is a diagram illustrating a FLASH™ restriction mapping method.

This invention provides a non-human mammal that produces the human Aβ peptide in its brain (and other tissues) instead of the Aβ peptide normally produced by that species of non-human mammal. A non-human mammal homozygous for a targeted APP gene produces the human Aβ peptide exclusively, i.e., it produces no native Aβ peptide. A non-human mammal heterozygous for a targeted APP gene produces both the human Aβ peptide and the native Aβ peptide.

The non-human mammal of this invention produces the human Aβ peptide exclusively by normal endogenous APP processing mechanisms. The APP undergoing such processing is advantageously expressed from genes having the normal copy number, and under the control of the endogenous APP expression control sequences. As a result, the APP in the non-human mammal of this invention is produced with the same developmental timing, same tissue specificity, and same rates of synthesis normally associated with native APP in the non-human mammal.

In the non-human mammal of this invention, the Aβ peptide produced is exclusively the human form, and it is produced at levels greater than the levels at which endogenous Aβ peptide is produced in control animals. The enhanced production of the Aβ peptide presumably results from the Swedish mutations exerting an effect on the normal APP processing mechanisms. Overexpression of, and increased pools of, APP are advantageously avoided.

APP has been shown to have a number of biological effects including inhibition of serine proteases, (Oltersdorf et al., Nature 341: 144–147 1989)), cellular growth regulation (Saito et al., Cell 58: 615–622 (1989)), and cell attachment (Breen et al., J. Neurosci. Res. 28: 90–100 (1991)). In addition, APP and secreted forms of APP have been shown to be neuroprotective when overexpressed in transgenic mice, possibly through stabilization of intracellular calcium levels (Mucke et al., Brain Res. 666:151–167 (1994); Mattson et al., Neuron 10:243–254 (1993)). This is significant, because increased pools of APP may interfere with Aβ-specific pathogenic processes in unpredictable ways or initiate pathogenic events unrelated to the Aβ peptide or AD.

A further advantage of the present invention is that, in the non-human mammals homozygous for the targeted APP gene, the enhanced levels of human Aβ peptide are obtained in vivo, in the absence of native non-human Aβ peptides. This is significant, because the native Aβ peptide may have different properties than does the human Aβ peptide. See, e.g., Otvos et al., Eur. J. Biochem. 211:249–257 (1993); and Bush et al., Science 265:1464–1467 (1994).

The gene-targeted non-human mammals of this invention may be used as tools or models to elucidate the role of human Aβ in AD pathology and symptomatology. The gene-targeted non-human mammals of this invention also may be used as assay systems to screen for in vivo inhibitors of amyloidogenic processing of APP to yield the human Aβ peptide in their brains, non-brain tissues, or body fluids (e.g., blood and cerebrospinal fluid).

The first step in producing a gene-targeted non-human mammal of this invention is to prepare a DNA targeting vector. The targeting vector is designed to replace, via homologous recombination, part of the endogenous APP gene sequence of a non-human mammal, so as to "humanize" the Aβ peptide-encoding part of the endogenous APP gene and introduce the Swedish mutations. The targeting vector is used to transfect a non-human mammalian cell, e.g., a pluripotent, murine embryo-derived stem ("ES") cell. In this cell, homologous recombination (i.e., the gene-targeting event) takes place between the targeting vector and the target gene. The mutant cell is then used to produce intact non-human mammals (e.g., by aggregation of murine ES cells to mouse embryos) to generate germ-line chimeras. The germline chimeras are used to produce siblings heterozygous for the mutated targeted gene. Finally, interbreeding of heterozygous siblings yields non-human mammals (e.g., mice) homozygous for the mutated targeted gene.

Targeting vectors for the practice of this invention can be constructed using materials, information and processes known in the art. A general description of the targeting vector used in this invention follows.

A targeting vector for use in this invention has two essential functions: (1) to integrate specifically (and stably) at the endogenous APP target gene; and (2) to replace a portion of exon 16 of the endogenous APP gene, thereby introducing the Swedish mutations and the mutations that convert the endogenous Aβ sequence to the human Aβ sequence. Those two essential functions depend on two basic structural features of the targeting vector.

The first basic structural feature of the targeting vector is a pair of regions, known as "arms of homology," which are homologous to selected regions of the endogenous APP gene or regions flanking the APP gene. This homology causes at least part of the targeting vector to integrate into the chromosome, replacing part (or all) the APP target gene, by homologous recombination.

Homologous recombination, in general, is the rearrangement of DNA segments, at a sequence-specific site (or sites), within or between DNA molecules, through base-pairing mechanisms. The present invention relates to a particular form of homologous recombination sometimes known as "gene targeting."

The second basic structural feature of the targeting vector consists of the actual mutation(s) to be introduced into the target gene. In the present invention, those mutations are nucleotide changes yielding the following amino acid changes: Gly to Arg (Aβ 5, APP 676); Phe to Tyr (Aβ 10, APP 681); Arg to His (Aβ 13, APP 684). The mutation(s) to be introduced into the APP target gene must be located within or between the arms of homology.

Gene targeting, which affects the structure of a specific gene already in a cell, is to be distinguished from other forms of stable transformation, wherein integration of exogenous DNA for expression in a transformed cell is not site-specific, and thus does not predictably affect the structure of any particular gene already in the transformed cell. Furthermore, with the type of targeting vector preferred in the practice of this invention (e.g., the one described below), a reciprocal exchange of genomic DNA takes place (between the arms of homology and the target gene), and chromosomal insertion of the entire vector is advantageously avoided.

The examples below describe the actual construction of an APP gene targeting vector (and its use) to mutate the murine Aβ peptide-encoding sequence so that it encodes the human Aβ peptide, and simultaneously to introduce the Swedish FAD mutations into the murine APP gene. One of ordinary skill in the art will recognize that numerous other targeting vectors could be designed to introduce the same mutations, using the principles of homologous recombination. Gene-targeted non-human mammals produced using such other targeting vectors are within the scope of the present invention. A discussion of targeting vector constraints and considerations follows.

The length of the arms of homology that flank the replacement sequence can vary considerably without significant effect on the practice of the invention. The arms of homology must be of sufficient length for effective heteroduplex formation between one strand of the targeting vector and one strand of a transfected cell's chromosome, at the APP target gene locus. Increasing the length of the arms of homology promotes heteroduplex formation and thus targeting efficiency. However, it will be appreciated that the incremental targeting efficiency accruing per additional homologous base pair eventually diminishes and is offset by practical difficulties in target vector construction, as arms of homology exceed several thousand base pairs. A preferred length for each arm of homology is 50 to 10,000 base pairs.

There is considerable latitude in the choice of which regions of the APP target gene, chromosomal regions flanking the APP target gene are represented in the targeting vector's arms of homology. The basic constraint is that the base pairs to be changed in the APP target gene must lie within or between the arms of homology. The arms of homology may lie within the APP target gene, but it is not necessary that they do so. They may flank the APP target gene.

Preferably, the targeting vector will comprise, between the arms of homology, a positive selection marker. The positive selection marker should be placed within an intron of the target gene, so that it will be spliced out of mRNA and avoid the expression of a target/marker fusion protein. More preferably, the targeting vector will comprise two selection markers: a positive selection marker, located between the arms of homology, and a negative selection marker, located outside the arms of homology. The negative selection marker is a means of identifying and eliminating clones in which the targeting vector has been integrated into the genome by random insertion instead of homologous recombination. Exemplary positive selection markers are neomycin phosphotransferase and hygromycin β phosphotransferase genes. Exemplary negative selection arkers are *Herpes simplex* thymidine kinase and diphtheria oxin genes.

To eliminate potential interference on expression of the target protein, the positive selection marker can be flanked by short loxP recombination sites isolated from phage P1 DNA. Recombination between the two loxP sites at the targeted gene locus can be induced by introduction of cre recombinase to the cells. This results in the elimination of the positive selection marker, leaving only one of the two short loxP sites. (See U.S. Pat. No. 4,959,317). Excision of the positive selectable marker from intron 15 is correlated with enhanced expression from the APP-targeted gene and as a consequence greater Aβ production. The enhancement of APP expression when the positive selectable marker is excised is most likely because the marker carries its own RNA processing signals that interfere with efficient and faithful APP transcription. Accordingly, animals containing the above-disclosed APP mutations but lacking the positive selectable marker are preferred for measuring human Aβ and screening for inhibitors of amyloidogenic processing of APP.

FIG. 1 illustrates general principles of gene targeting. In FIG. 1, mutations to be incorporated into the target gene are indicated by asterisks. In targeting vector (FIG. 1b), the arms of homology are regions from 1 to 2 and from 3–4. The arms of homology are placed in the vector on either side of (i.e., flanking) a DNA sequence encoding a positive selection marker. A gene encoding susceptibility to an otherwise nontoxic drug (negative selection marker) is placed outside the region of homology. When the targeting vector is transfected into cells and integrated into the target gene, with crossovers occurring in the desired regions, the positive selection marker is inserted into the genome between regions 2 and 3 in this example (making the transformed cells resistant to the positive selection agent) while the negative selection marker is excluded. To enrich for the desired recombinants, transfected cells are grown in a culture medium containing the positive selection agent to select for the presence of the positive resistance marker and the negative selection agent, to select for the absence of the negative resistance marker.

Mutations in the arms of homology may or may not be incorporated into the target gene as a result of homologous recombination, depending on where the crossovers take place. For example, when hypothetical double crossover "A" occurs (FIG. 1), i.e., both crossovers on one side of the mutations, the mutations are not incorporated into the target gene. When hypothetical double crossover "B" occurs (FIG. 1), i.e., with the mutations between the crossovers, the mutations are incorporated into the target gene.

For a general description of gene targeting, see, e.g., *Nature* 336:348 (1988). One of ordinary skill in the art will recognize that while the examples below disclose our most preferred strategy and targeting vector for the development of a gene-targeted murine model system, various methods for producing gene-targeted murine, and non-murine, non-human mammals are known, and other strategies and targeting vectors will be readily apparent. Furthermore, as new methods become available, additional strategies and targeting vectors will be apparent, and may be preferred. Accordingly, the following examples are not intended as, and are not to be construed as, limiting with respect to the disclosure or the scope of the claims. Other non-murine, non-human mammals are within the scope of the present invention.

It should be recognized from the foregoing discussion that the practice of the present invention requires a DNA clone comprising at least that region of the APP gene that includes the nucleotides to be replaced. Such necessary DNA clones may be obtained by a variety of means. The nucleotide sequence of the human APP gene is known. See, e.g., Kang et al. (supra); Goldgaber et al. (supra); Tanzi et al. (supra); and Robakis et al. (supra). The necessary DNA clones may be obtained, for example, by following the APP gene cloning methods set forth in the publications cited above. Alternatively, the published sequences can be used for the complete chemical synthesis of the desired DNA or the chemical synthesis of oligonucleotides that can be used as probes or PCR primers, as tools to obtain the necessary DNA by conventional techniques.

In order that the invention described herein may be more fully understood, examples are provided below. It should be understood that these examples are for illustrative purposes only and are not to be construed as limiting the invention in any manner. Throughout these examples, molecular cloning reactions, and other standard recombinant DNA techniques, were carried out according to methods described in Maniatis et al., *Molecular Cloning—A Laboratory Manual*, Cold Spring Harbor Laboratory (1982) or Sambrook et al., *Molecular Cloning—A Laboratory Manual, 2nd Ed.*, Cold Spring Harbor Press (1989), using commercially available enzymes, except where otherwise noted.

EXAMPLES

Example 1 - Cloning of Mouse APP exon 16 region.

The mouse APP genomic DNA was isolated from a phage library created from 129/Sv mouse DNA partially digested with Sau3A and cloned into the BamHI site of Lambda DASH™. Approximately 1.2×10⁶ recombinant bacteriophage were screened for the presence of APP sequences by hybridization with a 300 base pair (bp), radiolabelled APP-specific DNA probe. This probe was generated by polymerase chain reaction (PCR) amplification using primers ST41 (SEQ ID NO:1) and ST42 (SEQ ID NO:2), which hybridize to the 5' end of exon 15 and the 3' end of exon 17, respectively, on a human APP cDNA clone (FIG. 2). The amplified fragment was separated from other components of the reaction by electrophoresis on a 1.0% agarose gel, and purified using GeneClean®II (Bio 101, Inc., La Jolla, Calif.). Purified probe DNA was radioactively labelled with $^{32}$P-dCTP by the random primer method using a commercially available kit (Multiprime DNA Labeling System™; Amersham Life Sciences, Arlington Heights, Ill).

From this screen, seven clones were identified that hybridized to the APP probe (i.e., λAPP26, λAPP29, λAPP23, λAPP18, λAPP13, λAPP17, and λAPP32). These clones were purified by limiting dilution and plaque hybridization with the APP probe.

For each clone, DNA was prepared from bacteriophage particles purified on a CsCl gradient. Restriction maps were then generated for each of the cloned inserts using the FLASH™ Nonradioactive Gene Mapping Kit (Stratagene™ Inc., La Jolla, Calif.). The method is depicted schematically in FIG. 3. This method of restriction mapping involves completely digesting 10 μg of the phage DNA with NotI, which cleaves the vector at both ends of the cloned insert, leaving a T3 bacteriophage promoter attached to one end, and a T7 bacteriophage promoter attached to the other end. The NotI-digested DNA was then subjected to an EcoRI partial digest. The products of the partial digest were visualized by ethidium bromide staining, and transferred to a GeneScreen™ membrane (NEN Research Products, Boston, Mass.), by capillary transfer. The membrane-bound DNA was hybridized with an alkaline phosphatase-labelled oligonucleotide specific for the T3 promoter (supplied with FLASH™ kit). After hybridization, the membrane was washed and developed with a chemiluminescence-yielding substrate and exposed to X-ray film for approximately 60 minutes.

The oligonucleotide probes effectively label one end of the insert. By determining the positions of the bands on the X-ray film and calculating the DNA size for which they correspond, it was possible to determine the position of the EcoRI sites relative to the T3 end of the insert (FIG. 3). The first probe was then stripped from the membrane, and hybridization was repeated with a T7-specific probe, to determine the positions of the EcoRI sites relative to the T7 end of the insert. This process was repeated using the enzymes HindIII and XbaI. By comparing the restriction enzyme maps of the different overlapping clones a composite map was assembled. Of the seven original clones isolated, five independent clones were identified (FIG. 2).

Figure 4:
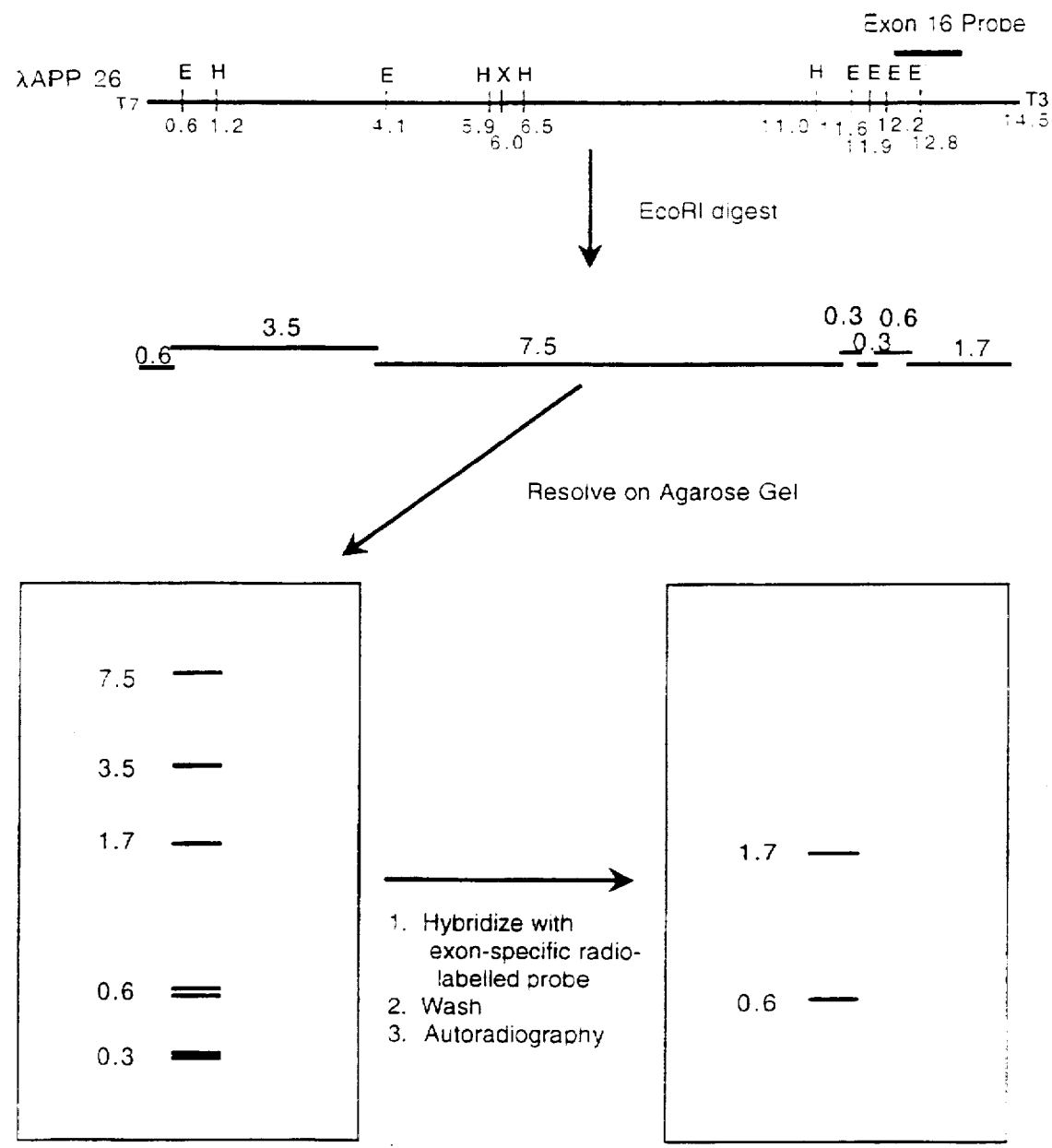
FIG. 4 is diagram illustrating the strategy for placing APP exons 15, 16 and 17 on the genomic APP restriction map.

Exons 15, 16 and 17 were next located on our restriction map by hybridizing exon-specific probes to complete digests of each of the five different lamda genomic clones. For example, 3 μg of DNA from each of the 5 different clones was completely digested with EcoRI. The digested DNA was resolved on a 0.8% agarose gel, visualized with ethidium bromide staining and transferred to a GeneScreen™ membrane (NEN Research Products, Boston, Mass.) by capillary transfer. The membrane-bound DNA was then hybridized with a DNA probe that specifically hybridized to sequences from mouse APP exon 16. This probe was generated by PCR using oligonucleotides ST47 (SEQ ID NO:3) and ST48 (SEQ ID NO:4), which hybridize to the 5' and 3' ends of exon 16 respectively. After hybridization, the membrane was washed and exposed to X-ray film (FIG. 4). This experiment revealed that all clones contained a 600 bp fragment that hybridized to the exon 16 probe. In addition, clone λAPP13 hybridized to a 5.1 kb fragment while clones λAPP18, λAPP26 λAPP23 yielded a fragment, in addition to the 600 bp fragment, of sizes 900 bp, 1.7 kb, and 3.6 kb respectively. By combining this information with the restriction map data for each lambda clone, exon 16 was placed on our map so that the EcoRI site in exon 16 (Yamada, et al., supra) corresponds to the EcoRI site at position 12.8 on our composite map. A similar procedure was used to identify the positions of exons 15 and 17 on our composite map, using exon 15 and exon 17-specific probes and utilizing the restriction enzymes XbaI and HindIII in addition to EcoRI. The exon 15-specific probe was generated using PCR primers ST45 (SEQ ID NO:5) and ST46 (SEQ ID NO:6). The exon 17-specific probe was generated using the primers ST49 (SEQ ID NO:7) and ST50 (SEQ ID NO:8). These last two 100 bp exons could only be localized to within the limits of a 4.4 kb fragment and a 1.9 kb fragment respectively (FIG. 2).

Example 2 - Construction of TarQetina Vector pAPP-TV

Figures 5A, 5B:
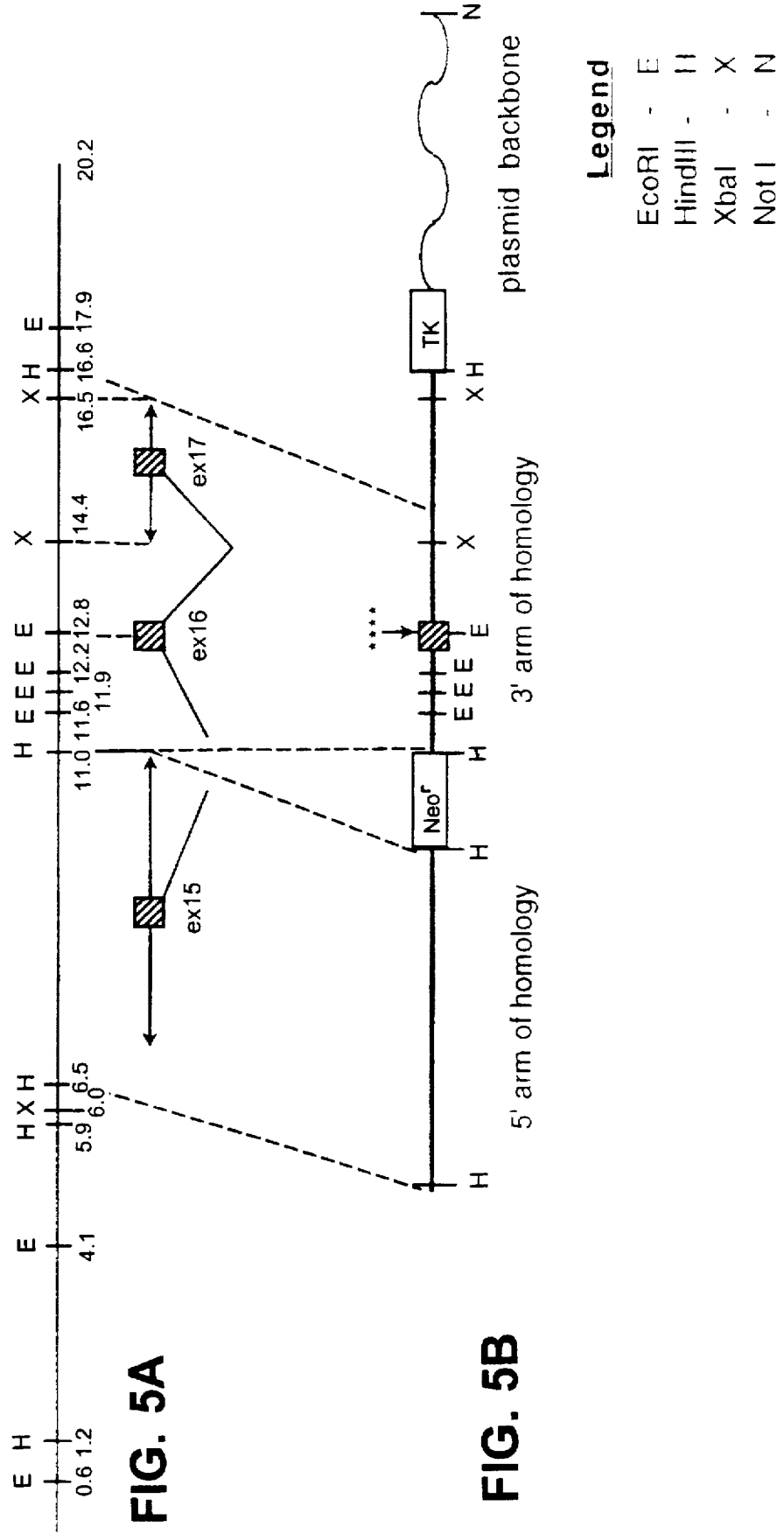
FIG. 5 is a pair of genetic maps illustrating the relationship between APP exon 16 and the pAPP-TV replacement vector. Single letter abbreviations for restriction endonucleases are as follows: E, EcoRI; H, HindIII; X, XbaI; and N, NotI.

A 4.5 kb HindIII fragment (position 6.5–11.0 on our summary map; FIG. 2) was chosen as a 5' arm of homology, and a 5.6 kb HindIII fragment (positions 11.0–16.6 on our summary map; FIG. 2) was chosen as a 3' arm of homology, which would contain the desired mutations. These fragments were isolated and cloned into pBlueScript™ SK+ (Stratagene, LaJolla, Calif.) and then subcloned into the plasmid pPNTlox$^2$ (described below) which contained a neo$^r$ gene, an HSV-TK gene and linker sequences to produce a replacement vector (pAPP-TV; FIG. 5). The vector of the example can contain loxP sites surrounding the neo$^r$ cassette, to allow for excision of the positive selection marker; see, e.g., Sauer U.S. Pat. No. 4,959,317, incorporated herein by reference.

Intermediate Plasmid pPNTlox$^2$

Figure 6:
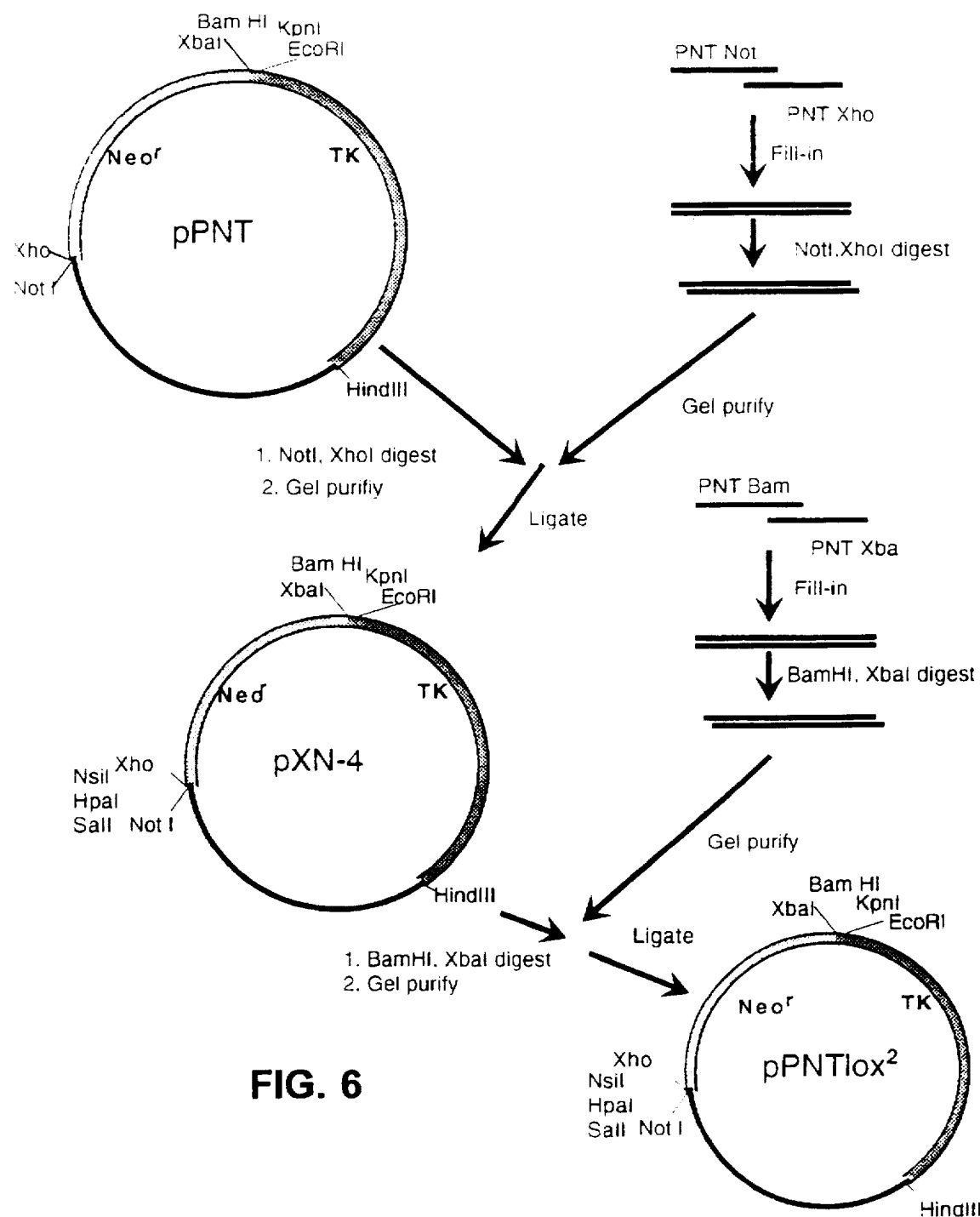
FIG. 6 is a schematic diagram illustrating the construction of plasmid pPNTlox$^2$.

The starting plasmid was pPNT (Tybulewicz, et al., *Cell* 65:1153–1163 (1991)); obtained from Dr. Richard Mulligan, MIT, Cambridge, Mass.). Two oligonucleotide linkers, one on each side of the neo$^r$ cassette, were inserted into pPNT to create the intermediate, pPNTlox$^2$ (FIG. 6). A double-stranded 79 bp 5' linker was created by annealing two single-stranded oligonucleotides that overlap at their 3' ends and then filling in the remaining single-stranded regions with the Klenow fragment of DNA polymerase I. The oligonucleotides PNT Not (SEQ ID NO:9) and PNT Xho (SEQ ID NO:10) (150 ng of each) were combined in a 30 μl reaction mixture containing 5 U of Klenow polymerase, Klenow polymerase buffer and 2 mM dNTPs (dATP, dCTP, dGTP, and dTTP). After incubation for 1 hour at 37° C., 5 μl of this reaction mixture was simultaneously digested with NotI and XhoI. In addition, 200 ng of pPNT was digested with NotI and XhoI. The digested plasmid was purified, using a 0.8% agarose gel, and treated with calf intestinal phosphatase according to standard methods. A quantity (66 ng) of the double digested linker was ligated to the double digested and phosphatase-treated pPNT DNA. Following DNA transformation of competent WM1100 *E. coli* with the ligated DNA (Dower, *Nucleic Acids Res.* 16:6127–6145 (1988)), plasmid DNA was isolated from ampicillin-resistant bacteria and subjected to restriction analysis. The desired recombinant plasmids were identified as having acquired SalI, HpaI and NsiI sites (present in the linker) while still retaining the NotI and XhoI sites of the starting plasmid. One such recombinant plasmid with a 79 bp linker sequence was identified and designated pXN-4 (FIG. 6).

A similar approach was used to insert a 40 bp 3' linker between the XbaI and BamHI sites of pXN-4. The oligonucleotides used to synthesize the linker were PNT Xba (SEQ ID NO:11) and PNT Bam (SEQ ID NO:12). In this case, pXN-4 and the double-stranded linker DNA were digested with XbaI and BamHI. The purified fragments were ligated and transfected into competent WM1100 bacteria. Plasmid DNA was digested with XbaI and BamHI, end-labelled with $^{32}$P-dCTP and Klenow polymerase, and resolved on an 8% acrylamide gel. The gel was dried and exposed to X-ray film. The desired recombinant clones were identified by a 40 bp band liberated by a XbaI-BamHI double digest. The resulting plasmid was designated pPNTlox$^2$ (FIG. 6). This construct includes the neo$^r$ cassette flanked by the loxP sequences (see, Sauer, supra).

To confirm the sequences of the inserted linkers, a fragment containing both linkers was isolated from pPNTlox$^2$ using NotI and EcoRI and cloned into pBlueScript™ SK+, for sequencing purposes. Identity of the linkers was confirmed by direct nucleotide sequencing (using T3 and T7 sequencing primers (Stratagene, La Jolla, Calif.) and Sequenase Version 2.0 DNA Sequencing Kit (United States Biochemical, Cleveland, Ohio).

Subcloning Arms of Homology

The HindIII fragment to serve as the 3' arm of homology was isolated from λAPP13 by digesting 30 μg of the phage DNA with HindIII, resolving the digested DNA on a 0.8% agarose gel, visualizing the DNA with ethidium bromide staining and then excising the 5.6 kb fragment from the gel. DNA was purified from the gel using GeneClean®II (Bio 101 Inc., La Jolla, Calif.). Simultaneously, 1 μg of pBlueScript™ SK+ (Stratagene, LaJolla, Calif.) was digested with HindIII and subsequently purified by the same procedure. Approximately 400 ng of the purified lamda DNA and 100 ng of the purified plasmid DNA were combined in a 10 μl ligation reaction, and competent WM1100 *E. coli* cells were transformed with the ligation products. Plasmid DNA from transformants was screened by restriction analysis, and plasmids, pAPP3'homol-7 and pAPP3'homol-4 (FIG. 7) were isolated.

Figure 7:
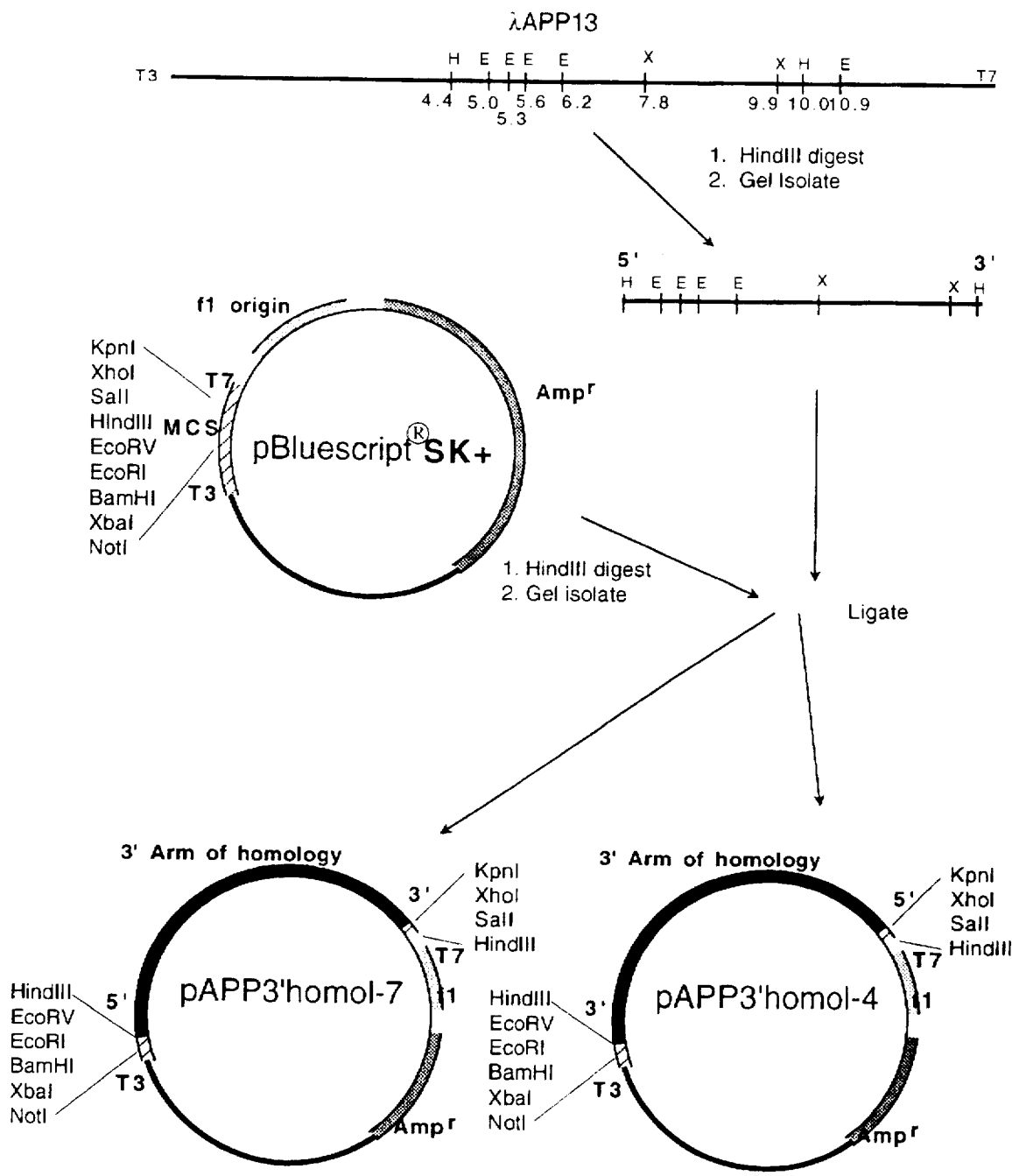
FIG. 7 is a schematic diagram illustrating the construction of plasmids pAPP3'homol-4 and pAPP3'homol-7.

These plasmids were analyzed after HindIII digestion to detect the 5.6 kb APP fragment. Since the insert could be in either of two orientations, plasmid DNA was further screened by XbaI digestion. Clone pAPP3'homol-4 had the APP insert oriented with the 5' end closest to the T7 promoter. In pAPP3'homol-7, the 5' end was next to the T3 promoter (FIG. 7).

Figure 8:
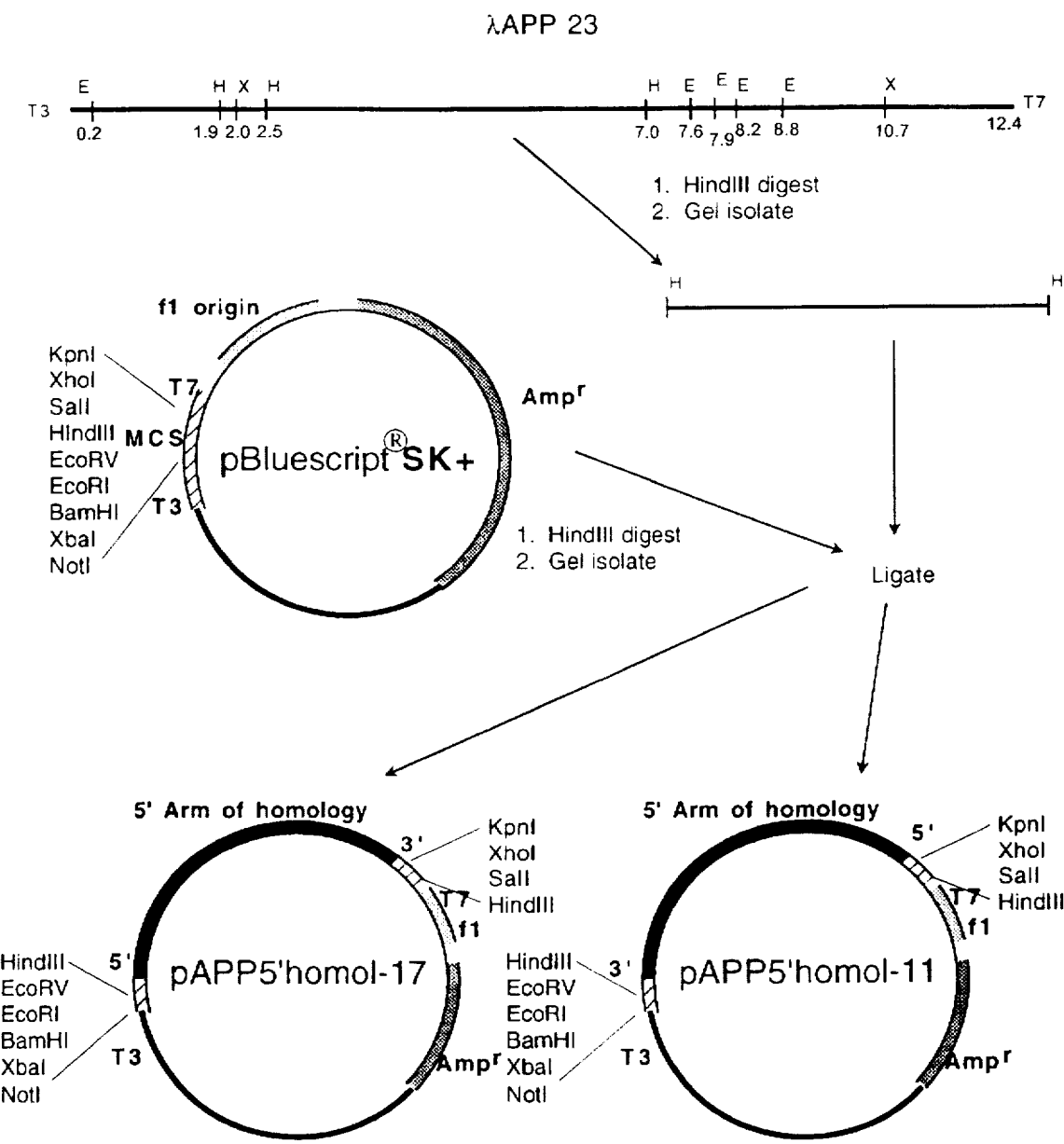
FIG. 8 is a schematic diagram illustrating the construction of plasmids pAPP5'homol-11 and pAPP5'homol-17.

The 5' arm of homology (a 4.5 kb HindIII fragment) was similarly subcloned from λAPP23 into pBlueScript™ SK+. The clone in which the 5' end of this arm of homology is juxtaposed to the T3 promoter was called pAPP5'homol-17, while the clone in which the 5' end of this arm of homology is adjacent to the T7 promoter was called pAPP5'homol-11 (FIG. 8).

Restriction Mapping of Arms of Homology

Figure 9:
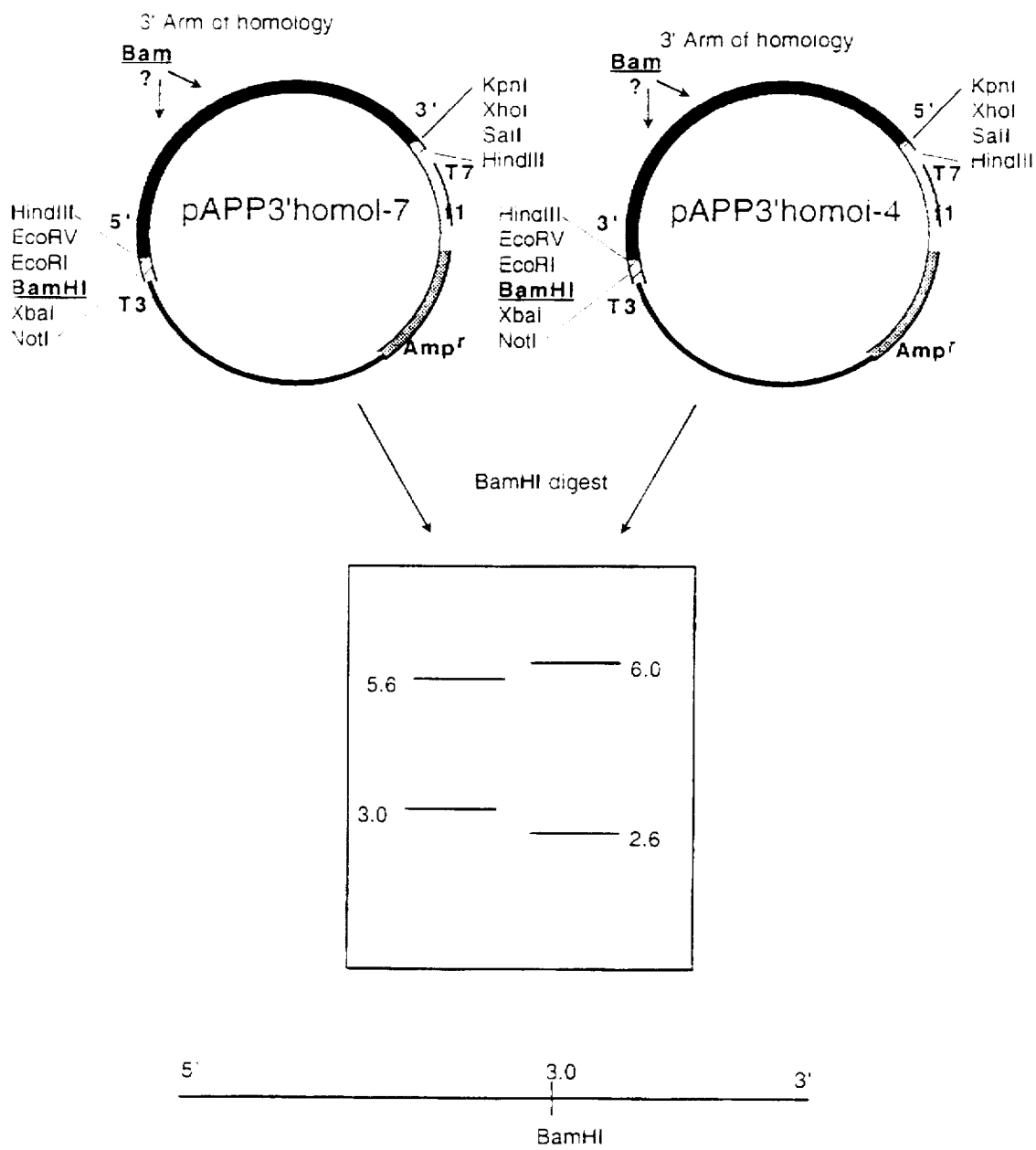
FIG. 9 is a schematic diagram illustrating the restriction mapping of the 3' arm of homology.

Further restriction enzyme mapping was performed on the 3' arm of homology. Plasmids pAPP3'homol-4 and pAPP3'homol-7 were digested with BamHI, and the resulting fragments were resolved on an agarose gel, stained with ethidium bromide and visualized. Since a BamHI site is in the pBlueScript™ SK+ plasmid, in the multiple cloning site, near the T3 promoter, it was possible to determine the position of the BamHI site in the 5.6 kb APP fragment by determining the fragment sizes in each of the two digested samples (FIG. 9).

Positions of restriction sites that occurred once or twice in the 5.6 kb APP fragment were determined by the above method. If more than two sites of a given enzyme were present it became necessary to determine the relative positions by double-digesting each of the two plasmids with the enzyme in question as well as an additional enzyme which cut at sites capable of resolving ambiguities. The list of additional enzymes used to characterize this region includes: AccI, ApaI, BamHI, BstXI, ClaI, EagI, EcoRV, HincII, HpaI, KpnI, NsiI, PstI, SacI, SalI, SmaI, SpeI, and XhoI. A summary of these data is in FIG. 10. The same procedures were used to create a restriction enzyme map for the 5' arm. (FIG. 10).

Fracment from 3' Arm of Homology

Figure 11:
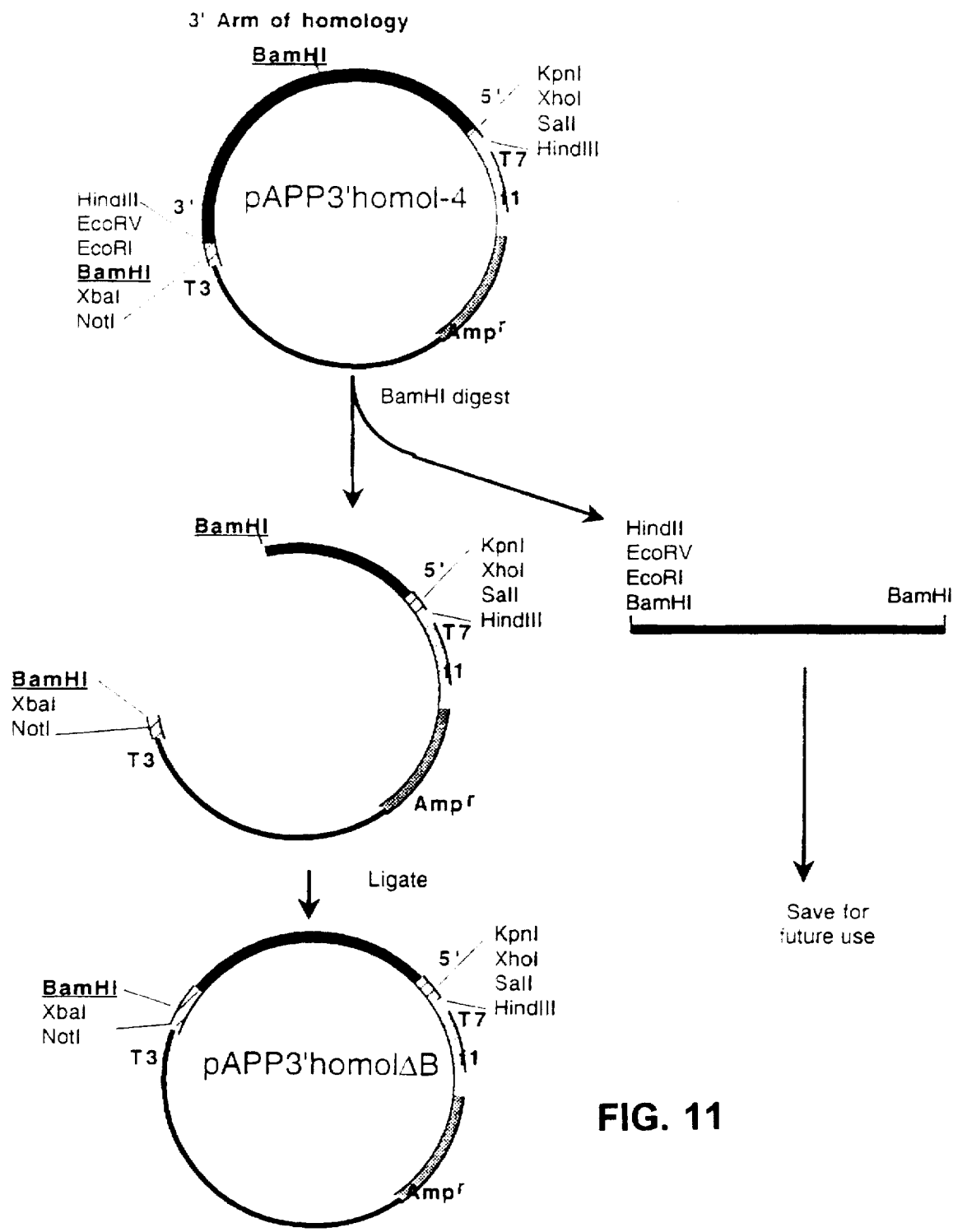
FIG. 11 is a schematic diagram illustrating the construction of plasmid pAPP3'homolAB.

For the PCR mutagenesis strategy described below, a fragment of the 3' arm was isolated. One μg of pAPP3'homol-4 was digested with BamHI to generate two fragments: a plasmid backbone carrying the first 3.0 kb of the 3' arm of homology and a 2.6 kb fragment representing the 3' half of the 3' arm of homology. Both fragments were isolated by gel electrophoresis. The 2.6 kb fragment was stored for later use. The 6.0 kb fragment that contained plasmid backbone attached to 3.0 kb of the arm of homology was re-ligated upon itself in order to generate a plasmid carrying the first 3.0 kb of the 3' arm. This plasmid was called pAPP3'homolΔB(FIG. 11).

Mutagenesis of 3' Arm of Homoloag

Figure 12:
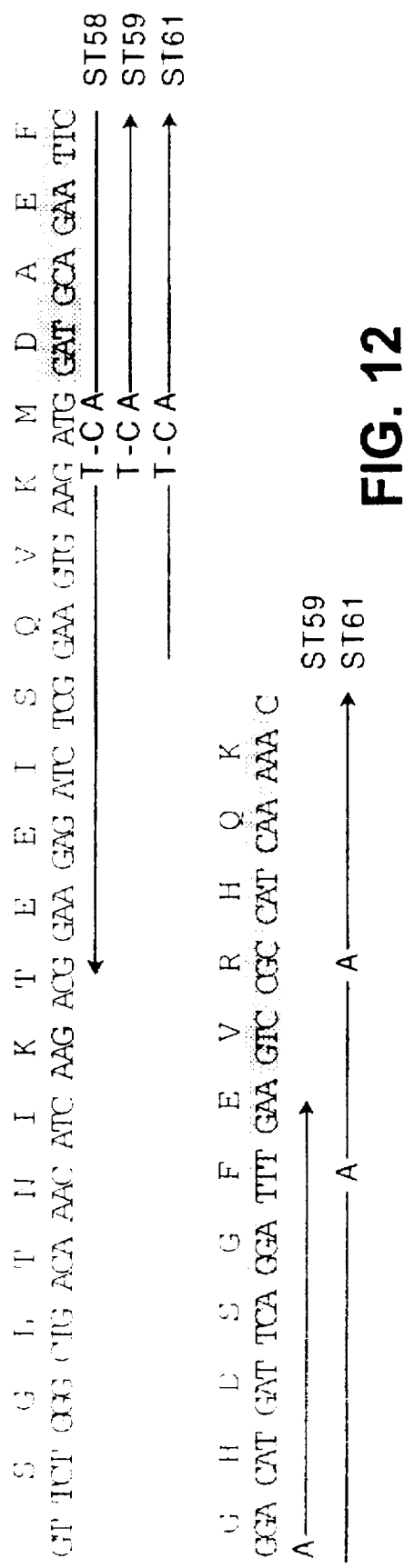
FIG. 12 is a partial sequence of mouse APP exon 16, showing amino acid changes.

A total of 6 base pair changes were introduced into exon 16, using a 2-step PCR strategy (see, FIG. 12). In the first step, the K670N/M671L mutation, an XbaI site, and the first base pair change of the humanizing mutations were introduced. This was accomplished by first linearizing pAPP3'homolΔB using the enzyme NaeI. Ten ng of the linearized DNA was then included in each of two PCR reactions. The first reaction contained the primers ST58 (SEQ ID NO:13) and T7 (Stratagene, La Jolla, Calif.). This generated a 1.4 kb band that encompassed the 5' end of the 3' arm of homology to the 5' junction of exon 16. This fragment also included the K670N/M671L mutation and a novel XbaI site that resulted as part of the K670N/M671L change.

Figure 13:
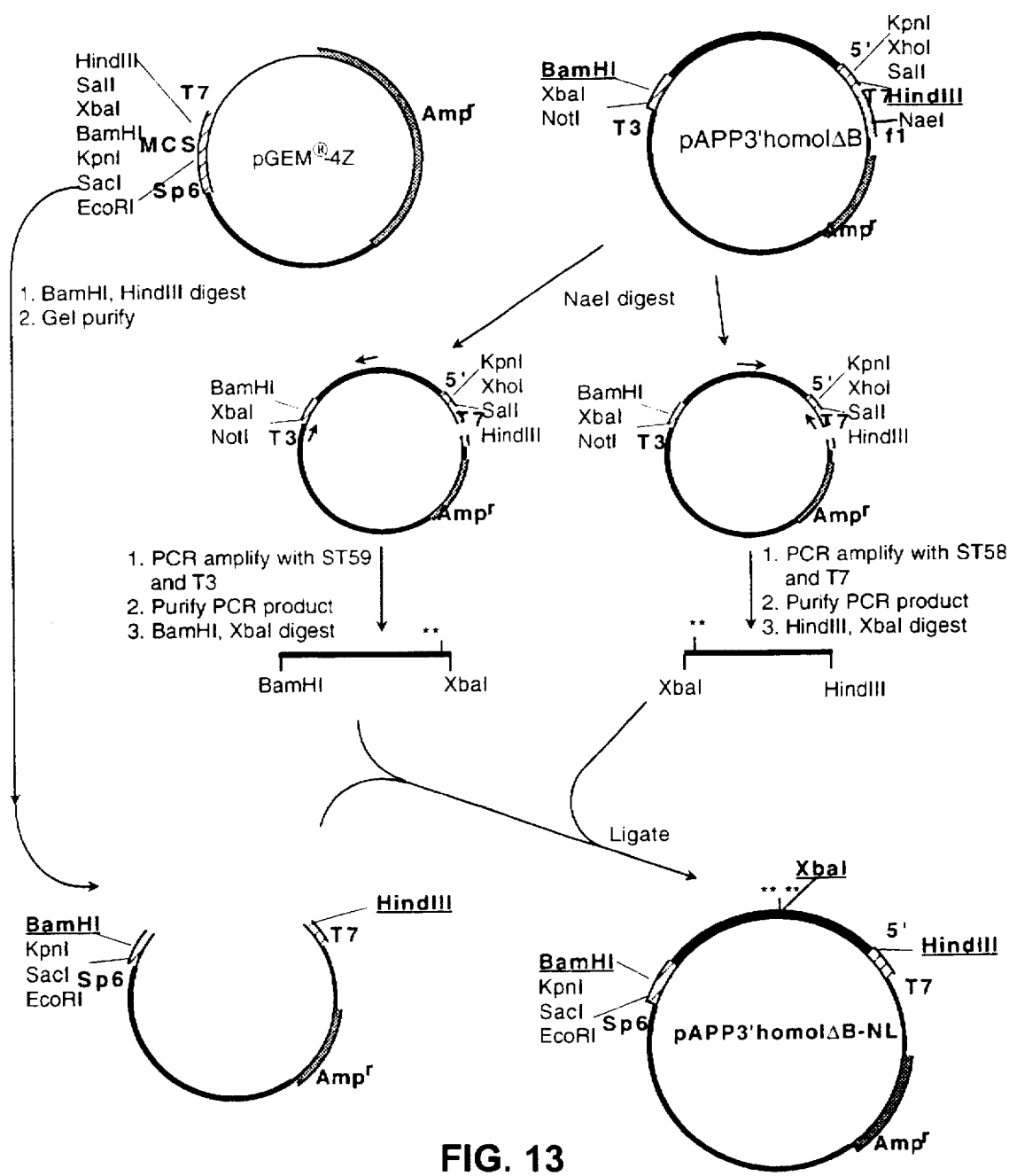
FIG. 13 is a schematic diagram illustrating the construction of plasmid pAPP3'homolAB-NL.

The second PCR reaction used the primers ST59 (SEQ ID NO:14) and T3 (Stratagene, La Jolla, Calif.). This generated a 1.6 kb fragment that encompassed all of exon 16 to the BamHI site located in the middle of the 3' arm of homology. This fragment also included the K670N/M671L mutation and XbaI site, as well as the first base pair change necessary to humanize Aβ (FIG. 13).

The product of the first reaction was purified using Magic™ PCR Preps DNA Purification System (Promega, Madison, WI) and digested with HindIII and XbaI in order to liberate the restriction sites at its ends. Similarly the product of the second reaction was purified and digested with XbaI and BamHI.

These two fragments, as well as HindIII and BamHI digested pGEM-4Z (Promega Corp., Madison, Wis.), were ligated and transfected into HB101 competent *E. coli* cells. DNA from the transformants was isolated and analyzed. A recombinant plasmid in which the two PCR fragments had joined at their XbaI sites and inserted into the BamHI and HindIII sites of pGEM™-4Z was designated pAPP3'homolΔB-NL (FIG. 13).

Figure 14:
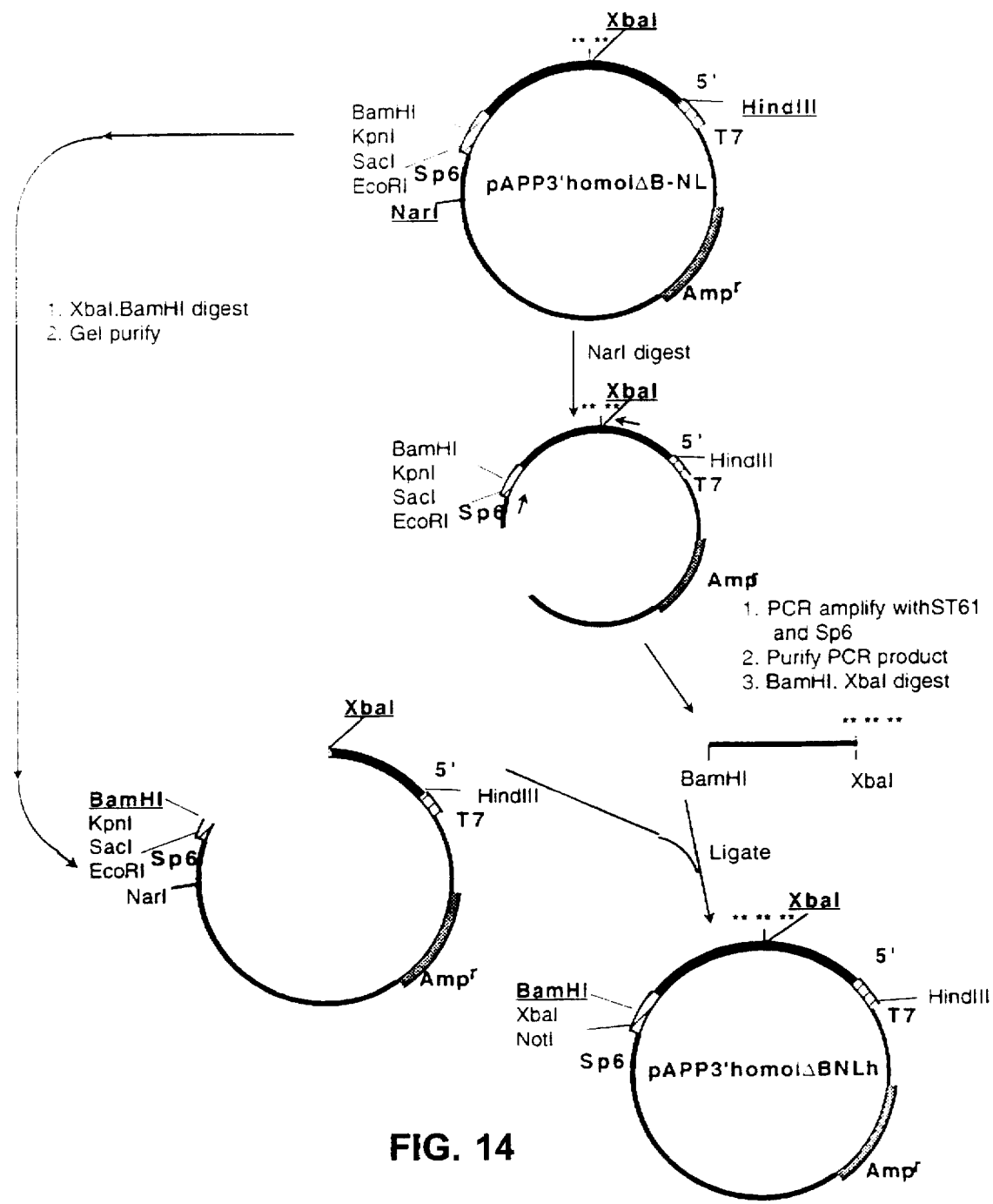
FIG. 14 is a schematic diagram illustrating the construction of plasmid pAPP3'homolAB-NLh.

Using a similar strategy, a final PCR step to introduce the remaining mutations into exon 16 was employed, in order to convert it to the human sequence. Plasmid pAPP3'homolΔB-NL was linearized with NarI. The linearized DNA was amplified by PCR, using primers ST61 (SEQ ID NO:15) and Sp6 (Promega, Madison, Wis.). The 1.6 kb purified DNA fragment was digested with XbaI and BamHI and ligated to the 4.4 kb XbaI, BamHI-digested p3'homoΔDB-NL DNA fragment which had been isolated by gel electrophoresis. The resulting plasmid was designated pAPP3'homolΔB-NLh (FIG. 14).

Figure 15:
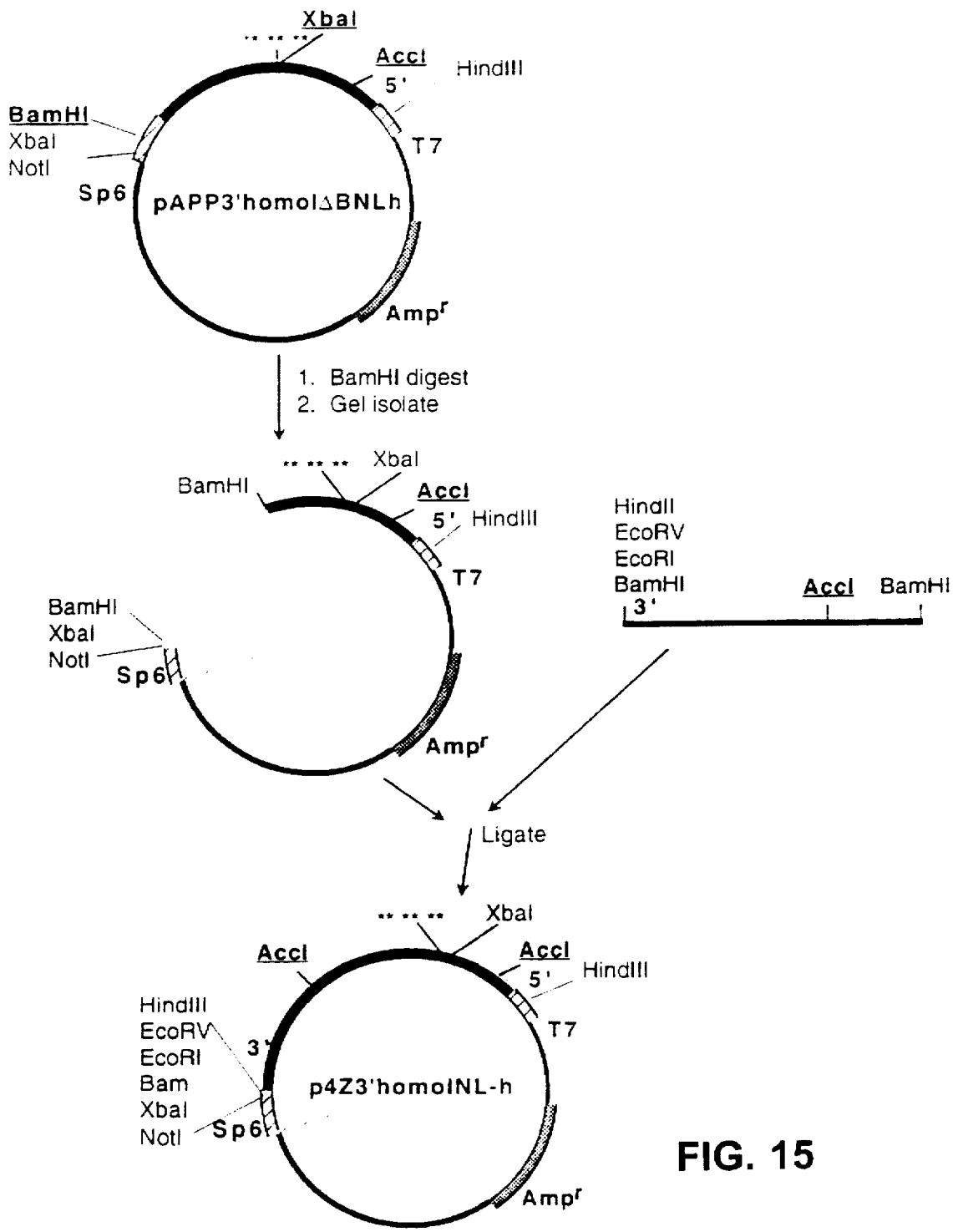
FIG. 15 is a schematic diagram illustrating the construction of plasmid p4Z3'homolNL-h.

To confirm the sequence of the mutagenized exon 16, direct nucleotide sequencing was performed, using the primers ST47(SEQ ID NO:3); which hybridizes to the 5' end of exon 16 and ST62(SEQ ID NO:16), which hybridizes to the intron region immediately 3' to exon 16. The 2.6 kb BamHI fragment, which was the 3' half of the 3' arm of homology, and which had been stored, was introduced back into the mutagenized half of the arm of homology. For this, plasmid pAPP3'homolΔB-NLh was linearized with BamHI and the previously purified 2.6 kb BamHI fragment was ligated to it. The 2.6 kb BamHI fragment could insert into the plasmid in either of two orientations. Proper orientation was determined by AccI digestion. The correctly oriented BamHI fragment yields a 3.8 kb fragment while the incorrect orientation yields a 4.6 kb fragment (FIG. 15). The proper recombinant plasmid was designated p4Z3'homolNL-h.

Figure 16:
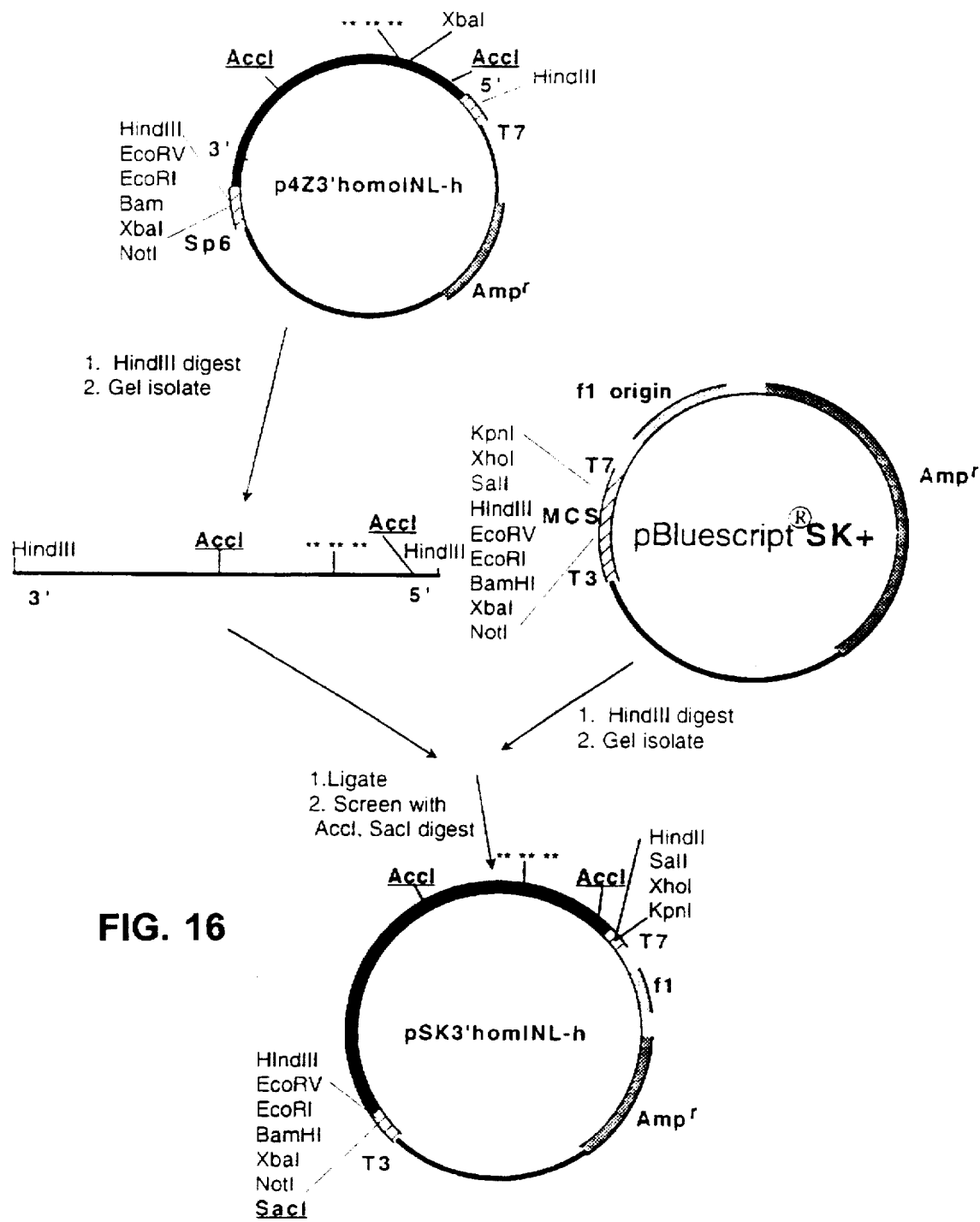
FIG. 16 is a schematic diagram illustrating the construction of plasmid pSK3'homolNL-h.

In order to introduce the necessary restriction sites at either end of the mutagenized arm of homology, the arm was next "shuttled" into the vector pBlueScript™ SK+. The plasmid p4Z3'homolNL-h was digested with HindIII, the resulting 5.6 kb band was isolated by gel electrophoresis and cloned into the HindIII site of pBlueScript SK+. The orientation of the insert was determined by double digesting plasmid DNA with the enzymes AccI and SacI. A recombinant plasmid was chosen in which the 5' end was adjacent to the T7 promoter. This plasmid is designated pSK3'homolNL-h (FIG. 16).

Assembling Targeting Vector pAPP-TV

Figure 17:
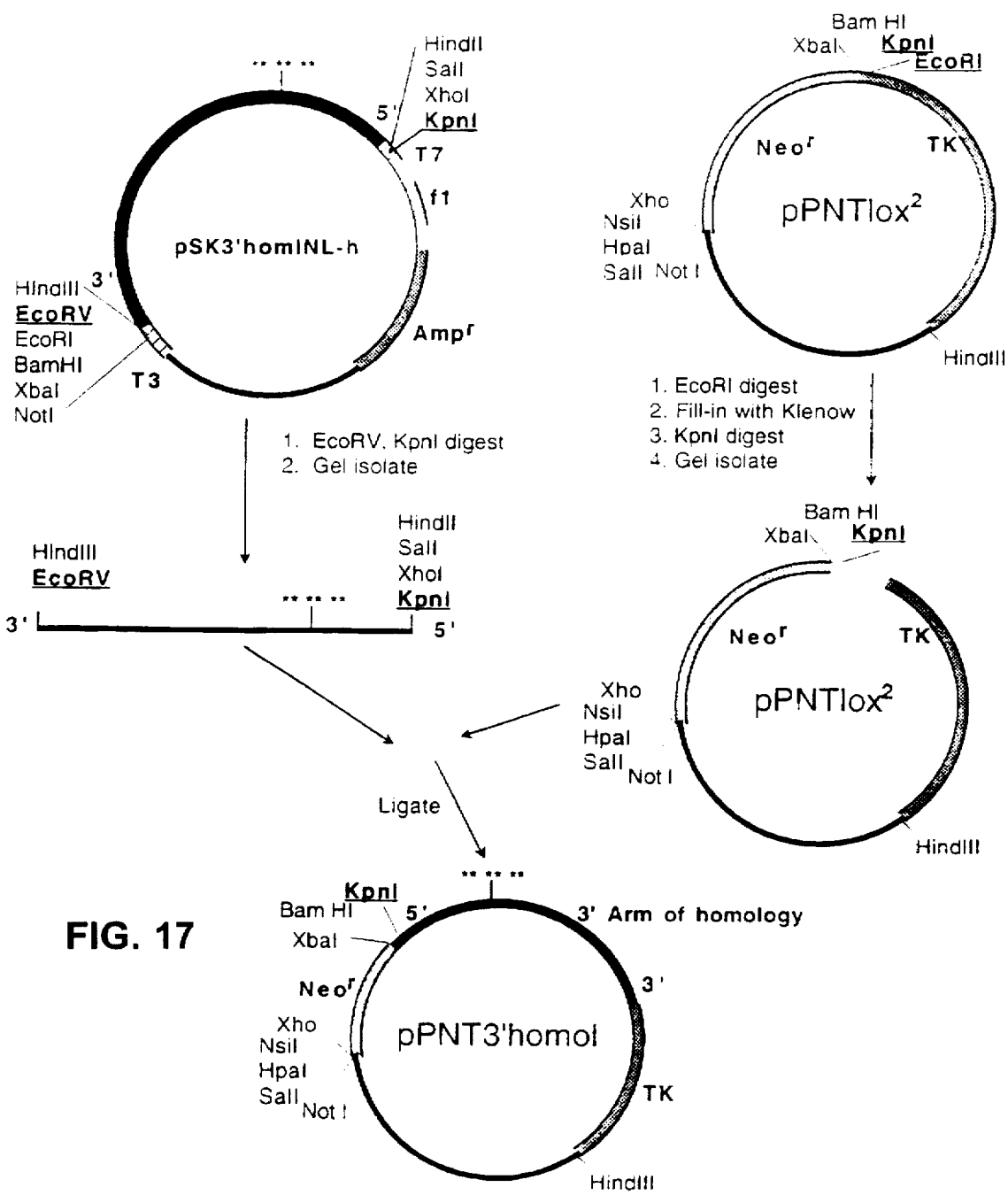
FIG. 17 is a schematic diagram illustrating the construction of plasmid pPNT3'homol.

The plasmid pPNTlox[2] was prepared to receive the 3' arm of homology by digestion with EcoRI and then filling in the 4 base overhang using Klenow polymerase. Following further digestion with KpnI, the plasmid was isolated by gel electrophoresis. The 3' arm of homology was prepared as a 5.6 kb EcoRV, KpnI fragment (also isolated by gel electrophoresis) and cloned into the purified and digested pPNTlox[2] DNA. The resulting plasmid was designated pPNT3'homol (FIG. 17).

Figure 18:
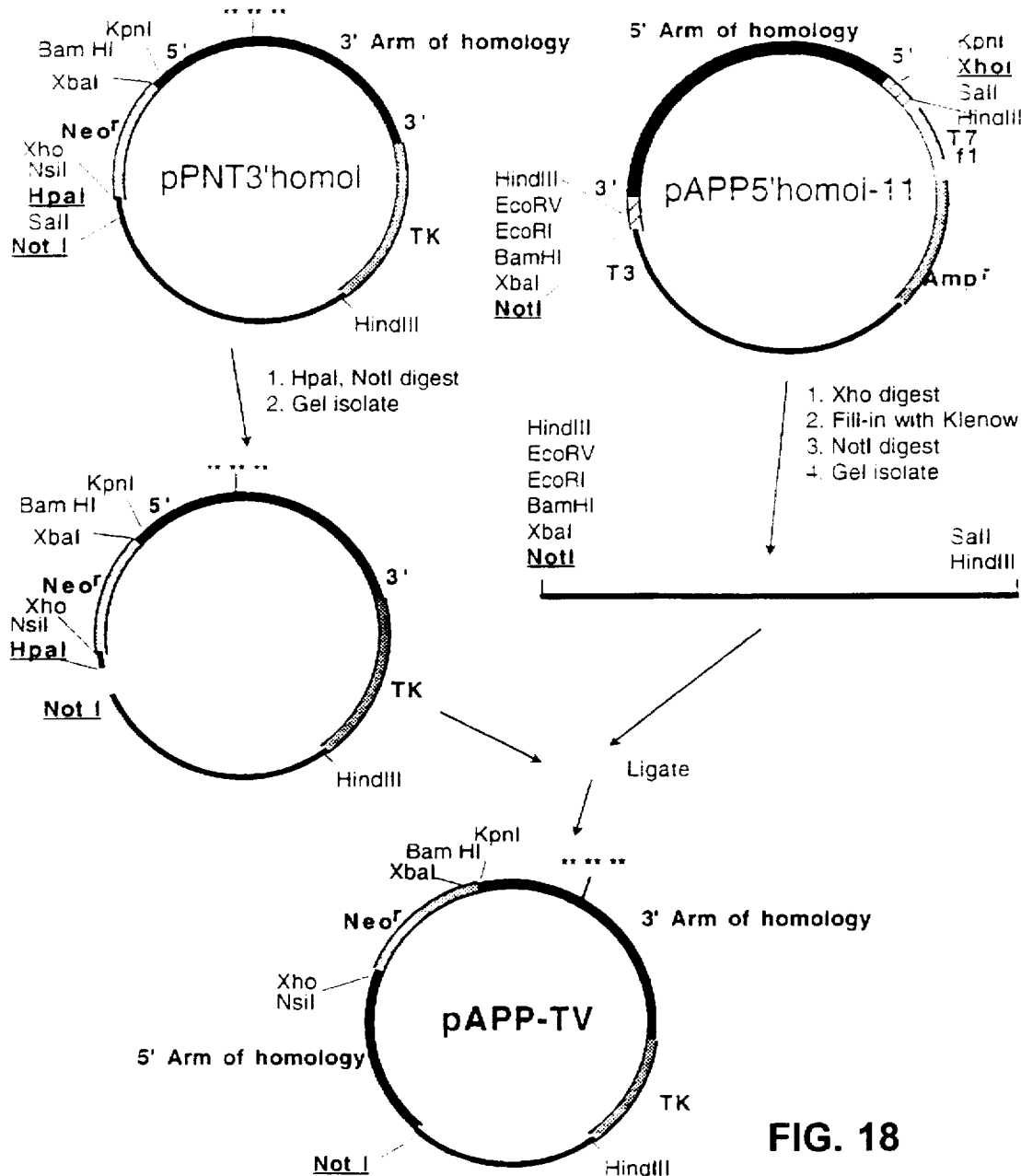
FIG. 18 is a schematic diagram illustrating the construction of plasmid pAPP-TV.
Figure 19A:
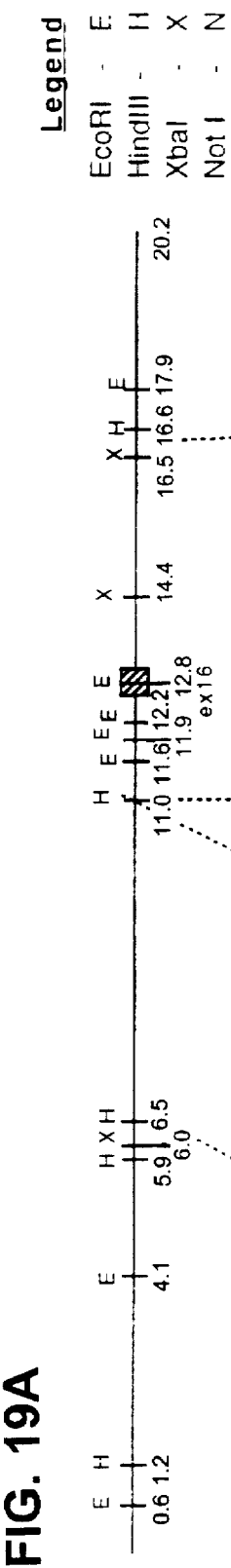
FIG. 19 is a schematic diagram illustrating the strategy to detect homologous recombination within mouse APP. Single letter abbreviations for restriction endonucleases are as follows: E, EcoRI; H, HindIII; X, XbaI; and N, NotI.
Figure 19B:
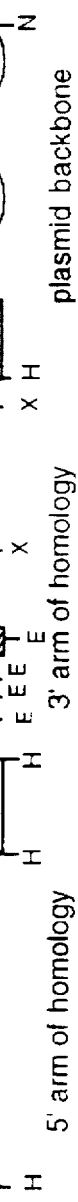
Figure 19C:
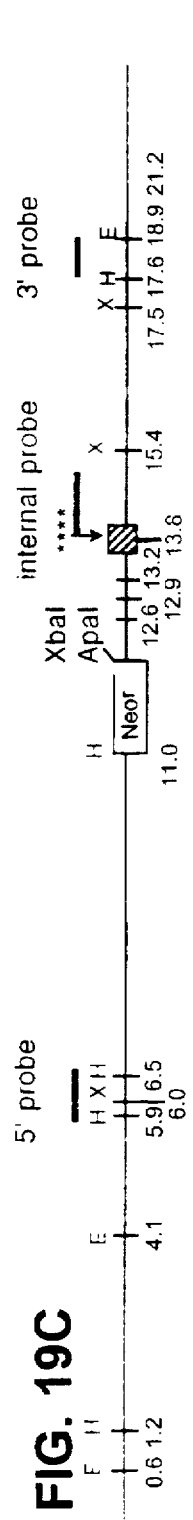
Figure 19D:
Figure 19E:
Figure 19F:

The 5' arm of homology was inserted into pPNT3'homol to give the final plasmid pAPPTV (FIG. 18). The 5' arm of homology was liberated by digesting plasmid DNA with XhoI, followed by filling-in the overhang with Klenow polymerase and then digesting with NotI. Plasmid pPNT3'homol was prepared by double digesting with NotI and HpaI. The two DNA fragments were ligated and transfected into competent WM1100 *E. coli* cells.

Example 3 - Mutagenesis of Mouse APP Gene in ES cells

The R1 line of ES cells derived from pigmented 129/Sv× 129/Sv-CP F1 hybrid mice (Nagy, et al., *Proc. Natl. Acad. Sci. USA* 90: 8424–8428 (1993)) incorporated herein by reference), was obtained from Dr. Janet Rossant, Dr. Andras Nagy, Reka Nagy, and Dr. Wanda Abramow-Newerly (Mt. Sinai Hospital, Toronto, Ontario, Canada). The cells were grown in ES cell medium consisting of Dulbecco's Modification of Eagle's Medium (with L-glutamine and 4.5 g/L glucose; Mediatech, Herndon, Va.) supplemented with 20% fetal bovine serum ("FBS"; Hyclone Laboratories, Logan, Utah; cat. # A-1115; Lot # 11152154), 0.1 mM non-essential amino acids (Mediatech 25-025-L1), 2 mM L-glutamine (Mediatech 25–005-L1), $10^6$M mercaptoethanol (Gibco 21985-023) 1 mM sodium pyruvate (Mediatech 25-000-L1), 1×concentration of a penicillin (5000 IU/ml) streptomycin (5000 mcg/ml) solution (Mediatech 30-001-L1) and 1000 U/ml of leukemia inhibitory factor (Gibco BRL 13275-029). The cells were grown on tissue culture plastic plates that had been treated with a solution of 0.1% gelatin (Sigma G9391) (gelatinized plates).

The cultures were grown in 100×15 mm plastic petri plates and were passaged every 48 hours, or when the cells became about 80% confluent. For passage, the cells were washed with phosphate buffered saline (without $Ca^{2+}$ and $Mg^{2+}$) ("PBS") and then treated with a trypsin/EDTA solution (0.05% trypsin, 0.02% EDTA in PBS). After all of the cells were in suspension, the trypsin digestion was stopped by the addition of ES cell medium. The cells were collected by centrifugation and resuspended in 5 ml of ES cell medium. A 1 ml aliquot of the cell suspension was used to start a new plate of the same size.

Transfection of ES Cells

Plasmid DNA (400 µg) from PAPP-TV was prepared for electroporation by digesting it with Not I in a 1 ml reaction volume. The DNA was then precipitated with ethanol, washed with 70% ethanol, and resuspended in 500 µl of sterile water.

The NotI-linearized pAPP-TV DNA was electroporated into ES cells using a Bio-Rad Gene Pulser System (Bio-Rad, Hercules, Calif.). In each of 10 electroporation cuvettes, 40 µg of DNA was electroporated into $2.5 \times 10^6$ cells suspended in ES cell medium. The electroporation conditions used (250V and 500 µF) typically result in time constants ranging from 6.0 to 6.1 seconds. After electroporation, the cells were incubated for 20 minutes at room temperature in the electroporation cuvettes. The electroporated cells were then pooled and distributed equally onto 10 gelatinized plates. After 24 hours, the medium was aspirated and fresh ES cell medium was added. The next day, the medium in nine plates was replaced with ES cell medium supplemented with 150 µg/mL of G418 (Gibco) and 0.2 µM ganciclovir (Syntex, Palo Alto, Calif.) while one plate received medium supplemented only with 150 µg/mL of G418. After an additional 8 days of incubation, individual ES cell colonies were picked off the plates and separately expanded in a well of 24 well plates as described by Wurst et al. (*Gene Targeting Vol.* 126 (Joyner, ed.), IRL Press, Oxford Univ. Press, pp. 33–61 (1993)). Comparison of the number of colonies that grew on the plates supplemented with G418 and ganciclovir versus the number that grew with only G418 supplementation was used to determine the efficiency of negative selection.

Analyses of ES cell transformants

When the cell culture in each well of the 24-well plates became approximately 80% confluent, it was washed and the cells were dispersed with two drops of trypsin-EDTA. Trypsinization was stopped by the addition of 1 ml of ES cell medium. An aliquot (0.5 ml) of this suspension was transferred to each of two wells of separate 24-well plates. After the cells had grown to near confluence, one of the plates was used for cryopreservation of the cell line while the other was used as a source of DNA for each of the cloned cell lines.

For cryopreservation, the cells in a 24-well plate were chilled by placing the plate on ice. The medium was replaced with fresh ES cell medium supplemented with 10% DMSO and 25% FBS, and the plate was cooled at approximately 0.5° C. per minute, by insulating the plate in a styrofoam box and placing it in a −70° C. freezer.

To isolate the DNA from the clones on the other plate, the medium in each well was replaced with 500 µl of digestion buffer (100 mM Tris-HCl, pH8.5, 5 mM EDTA, 0.2% SDS, 200 mM NaCl, 100 µg/ml proteinase K). After overnight incubation at 37° C., 500 µl of isopropanol was added to each well and the plate was agitated for 15 minutes on an orbital shaker. The supernatant fluid was aspirated and replaced with 500 µl of 70% ethanol and the plate was shaken for an additional 15 minutes. The DNA precipitate was collected from the well and dissolved in 50 µl of TE solution (10 mM Tris-HCl pH 7.5, 1 mM EDTA).

The primary analysis for mutagenesis of the mouse APP gene involved a Southern hybridization screen of XbaI digested ES cell DNA. The 600 bp probe for this analysis was isolated from λAPP26 DNA digested with HindIII (FIG. 19). For the Southern hybridization screen, an aliquot (10 µl) of each ES cell line DNA was digested with ApaI, resolved on an 0.8% agarose gel, and transferred to a GeneScreen™ membrane. The probe was labelled with $^{32}$P-dCTP by random priming and hybridized overnight to the membrane at 58° C. (Church et al., *Proc. Natl. Acad. Sci. USA* 81:1991–1995 (1984)). An ES cell line in which the APP gene has undergone the desired homologous recombination yields a 9.8 kb and 5.5 kb fragment in this assay (FIG. 19). This because homologous recombination introduces a novel XbaI site into the region where the neo$^r$ cassette is incorporated. The 9.8 kb band results from the normal cellular copy of APP, while the 5.5 kb band results from the APP copy in which the novel XbaI site produces a shorter fragment. In this screen 22 cell lines (out of 248) were identified as potentially containing successfully targeted genes.

All of the cell lines scored as putative homologous recombinants by the primary screen were then further screened using a 300 bp probe isolated by first recovering a 3.2 kb EcoRI-SalI fragment from λAPP32 (FIG. 2) and then further isolating the 300 bp probe from an EcoRV digest of the EcoRI-SalI fragment. This probe was hybridized to ApaI digested ES cell DNA. In this case, the normal APP gene yielded a 17 kb ApaI fragment and the mutant APP gene an 8 kb fragment (FIG. 19). Of the 22 cell lines examined in this screen, nine were shown to have undergone homologous recombination at the 3' end.

Cell lines that were identified as having undergone homologous recombination by both screens were considered to have undergone bona fide homologous recombination. Depending on where the crossover occurs in the 3' arm of homology, the mutations, may or may not incorporate into the gene (FIG. 1). We therefore carried out Southern hybridizations to detect the novel XbaI site associated with the K670N/M671L mutation. For this, we used a 1.0 kb EcoRI-PstI fragment from p3'homolΔB (FIG. 10) to probe XbaI digested DNA. An unaltered APP gene yields an 9.8 kb band. An APP gene in which homologous recombination has taken place, but in which the planned mutations were not incorporated, yields a 3.7 kb band, while the inclusion of the desired mutations results in a 2.0 kb band. Of the nine bona fide homologous recombinant cell lines examined, four had incorporated the novel XbaI site.

DNA sequence analysis confirmed that the four cell lines with the novel XbaI site had each of the desired mutations. The DNA primers ST47 and ST62 were used to PCR amplify exon 16 from the mutant cell lines. The PCR products were purified using Magic™ PCR Preps DNA Purification System (Promega, Madison, Wis.) and cloned into pGEM®T (Promega, Madison, Wis.) according to the vendor's instructions. Theoretically, one half of the clones produced by this method will contain a PCR-amplified fragment from the non-mutagenized copy of exon 16. Clones carrying a mutagenized exon 16 were identified by the presence of an XbaI site in the cloned insert. DNA sequence analysis was then carried out using T7 and Sp6 primers (Promega, Madison, Wis.) and Sequenase Version 2.0 DNA Sequencing Kit (United States Biochemical, Cleveland, Ohio). All four cell lines (73, 89, 139, and 148) which carried the exon 16 XbaI site had all of the desired mutations.

The mutagenized APP gene described here was designated $APP^{nNLh}$ (wild-type APP gene is $APP^+$). The four ES cell lines bearing one copy of $APP^{nNLh}$ were designated APP73, APP89, APP139, and APP148. Three of these lines were thawed, propagated, and used to produce chimeric mice.

Example 4 - Production of APP Gene-Targeted Mice

APP mutant ES cells were used to make chimeric mice by aggregating the mutant ES cells to E2.5 embryos and transferring the aggregated embryos to pseudopregnant females (Wood, et al., *Nature* 365:87–89 (1993)). ES cells were prepared for aggregation by limited trypsinization to produce clumps that average 10–15 cells. E2.5 embryos were collected from superovulated CD-1 female mice by oviduct flushing, as described by Hogan et al. (*Manipulating the Mouse Embryo: A Laboratory Manual*, Cold Spring Harbor Laboratory, Cold Spring Harbor, N.Y. (1986)). The zona pellucida was removed from the embryos using acidic Tyrode's solution (Sigma Chemical Co., St. Louis, Mo). Aggregation wells were created by pressing a blunt metal instrument (a darning needle) into tissue culture plastic. Embryos were then placed in a well with a clump of approximately 10–15 ES cells in a small drop (approximately 20 µl) of M16 medium (Sigma Chem. Co., St. Louis, Mo.) under mineral oil. After an overnight incubation (37° C., 100% humidity, 5% $CO_2$ in air), the aggregate embryos were transferred to the uterine horns of a pseudopregnant female. Contribution of the ES cells to the offspring was scored by the appearance of pigmented coat color. Pigmented mice are termed chimeric founders. Germline contribution by the ES cells was scored by the appearance of pigmented offspring from a cross between the chimeric founders and CD-1 females.

Of three mutant APP ES cell lines used in embryo aggregations, one gave two germline chimeras (Table 1).

TABLE 1

| Cell Line No. | Number of Embryo Aggregation | Number of Pups Born | Number of Chimeric Founders | Number of Germline Chimeras |
|---|---|---|---|---|
| APP73 | 143 | 12 | 2 | 0 |
| APP139 | 79 | 15 | 8 | 2 |
| APP148 | 140 | 19 | 8 | 0 |

The germline chimeras were used to establish lines of mice carrying $APP^{nNLh}$. The presence of the mutant APP allele in the pigmented offspring was determined by Southern analysis (as described above) with genomic DNA prepared from a tail sample. Mice heterozygous for $APP^{nNLh}$ ($APP^{nNLh}/APP^+$) have 8.8 kb and 2.0 kb XbaI fragments that hybridize with the 1.0 kb EcoRI-PstI probe. Mice homozygous for the mutant APP allele ($APP^{nNLh}/APP^{nNLh}$) were established by crossing two heterozygous mutant APP mice and were identified as having only a 2.0 kb XbaI genomic DNA fragment that hybridized with the 1.0 kb EcoRI-PstI probe.

Example 5 - Excision of the neo cassette

To remove the neo gene from intron 15 of the APP-targeted ES cells, 10 µg of circular pBS185 plasmid DNA (Sauer et al. *New Biol.* 2:441–449 (1990)) encoding the Cre recombinase was electroporated into the APP139 ES cell line using conditions described in example 3 except that only 700 ES cells were in the electroporation cuvette. After 20 minutes recovery at room temperature all of these cells were plated onto a gelatinized plate and grown in ES cell medium in the absence of G418 selection. Medium was changed every 48 hours. After 8 days, individual colonies were picked into 24 well plates and expanded. DNA was prepared from the expanded cell lines as described (Wurst et al., *Gene Targeting*, (Joyner, ed.), Oxford Univ. Press, Oxford, England, pp. 33–61 (1993)). Loss of the PGK/neo gene was detected by Southern hybridization using the 300 bp EcoRI-EcoRI fragment from p3'homolAB to probe XbaI digested DNA (see FIG. 10). An unaltered APP gene yields a 9.8 kb band, an altered APP gene in which the APP mutations and the $neo^r$ gene are incorporated yields a 2.0 kb band, and an APP gene in which the $neo^r$ gene has been excised, but the APP mutations remain incorporated, yields a 7 kb band. A total of 149 clones were screened, and 5 excision clones ($neo^-$) were identified.

A chimeric founder mouse produced by embryo aggregation with one of these $neo^-$ clones (APP139-34) exhibited germline transmission of the mutant APP allele (termed $APP^{NLh}$). From this founder, heterozygous ($APP^{NLh}/APP^+$) and homozygous ($APP^{NLh}/APP^{NLh}$) lines for the $neo^-$ APP mutant allele were established.

Example 6 - Expression of Humanized APP in Targeted ES Cells

Figure 20:
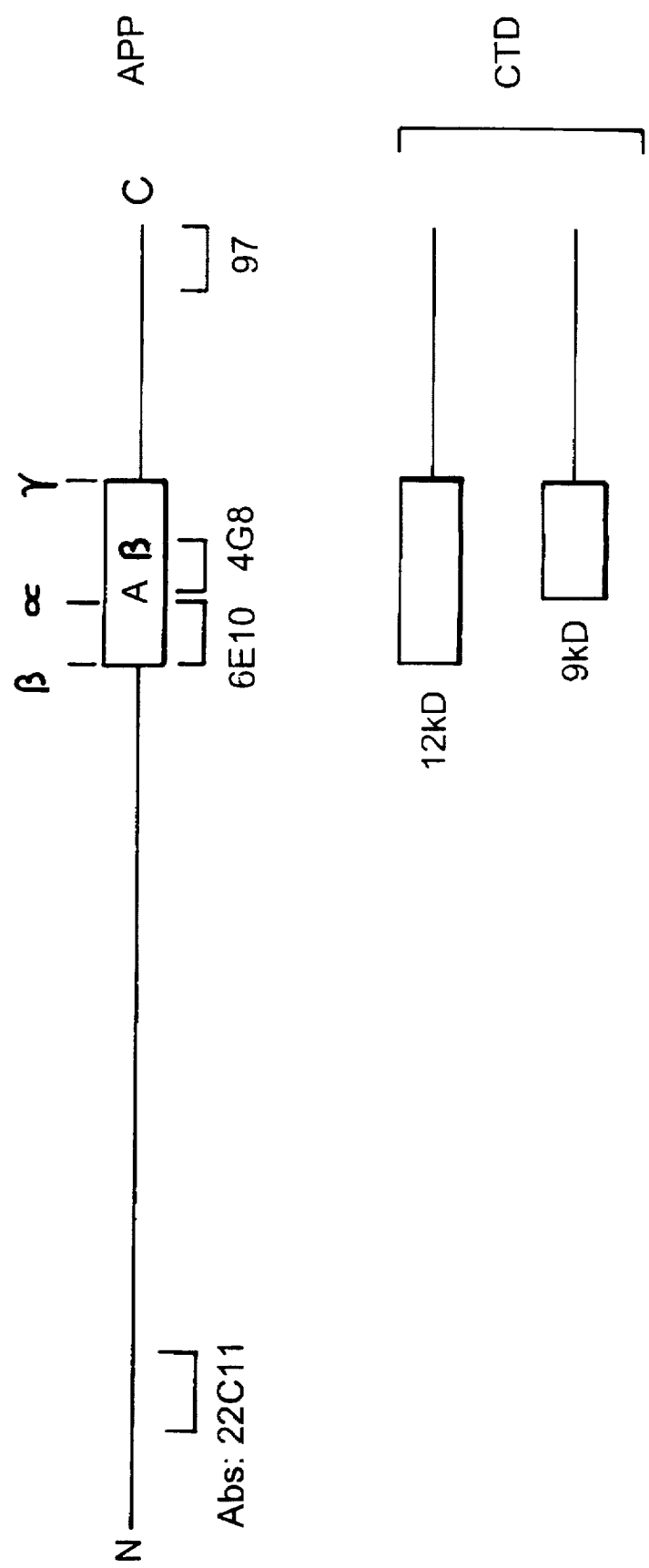
FIG. 20 is a schematic diagram of APP, relevant carboxyl-terminal derivatives (CTD) and APP-specific antibodies.

To determine if APP-targeted ES cell lines express full length APP containing the humanizing mutations in the Aβ domain, immunoblot analysis was done. ES cell lines 139, 89, and 73, along with the parental R1 ES cell line, were individually cultured in ES cell medium. After cells reached 80% confluence, the medium was changed to ES cell medium lacking serum and the cells were maintained at 37° C. for 4 hours. Medium was collected and the proteins were concentrated by precipitation with 10% trichloroacetic acid (TCA), resuspended in 1×SDS sample buffer (Laemmli, *Nature* 227:680–685 (1970)) and boiled for 5 minutes. Samples were electrophoresed on 6% SDS-polyacrylamide gels and electroblotted onto nitrocellulose (Towbin et al., *Proc. Natl. Acad. Sci USA* 76:4350 (1979)). Filters were blocked with 5% nonfat evaporated milk in Tris-buffered saline (TBS) (150 mM NaCl, 20 mM Tris-HCl, pH 7.4), followed by incubation with either antibody 6E10 (Kim et al., *Neurosci. Res. Commun.* 7:113–122 (1990))(1:2000) or antibody 22C11 (Weidemann et al., Cell 57:115–126 (1989)) (1:300). Antibody 6E10 (FIG. 20) was raised against residues 1 to 17 of the human Aβ peptide and has been shown to recognize human, but not rodent APP (Buxbaum et al., *Biochem. Biophys. Res. Commun.* 197:639–645 (1993)). Antibody 22C11 (FIG. 20) was raised against a peptide consisting of residues 60 to 100 of APP and recognizes human and rodent APP equally. Filters were incubated with goat anti-mouse IgG conjugated to horseradish peroxidase (1:2000) (BioRad), followed by detection with enhanced chemiluminescence (ECL, Amersham).

Figure 21:
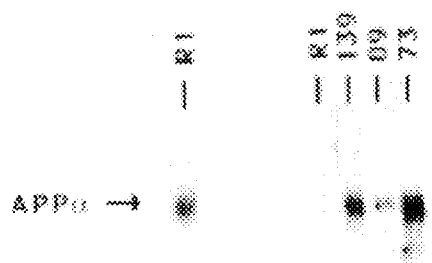
FIG. 21 is a photograph of an immunoblot used to detect human Aβ epitopes from targeted ES cells.

The immunoblot results (FIG. 21) show that parental R1 cells synthesize an APP species that reacts with antibody 22C11 but not the human-specific 6E10 antibody. In contrast, the APP-targeted ES cell lines 139, 89 and 73 express and secrete an APP species that is recognized by antibody 6E10. This indicates that these cell lines express an APP protein containing the humanizing mutations present within the first 17 amino acids of the Aβ domain.

Example 7 - Expression of Humanized APP in Mouse Brain

Heterozygous APP-targeted mice (APP$^{nNLh}$/APP$^+$) derived from ES cell line 139 were used to test for the expression of the humanized APP in their brain cells. A heterozygous (APP$^{nNLh}$/APP$^+$) APP-targeted mouse and a littermate control mouse (APP+/APP +) were sacrificed at 2 months of age, and their brains were removed. Neocortex (ctx), hippocampus (hp), and cerebellum (Cb) were dissected from each fresh brain and subsequently frozen on dry ice. Approximately 50 mg of each tissue and ~50 mg normal human frontal cortex, were each sonicated in 0.2 ml of 150 mM NaCl, 50 mM Tris-HCl (pH 8), 1% Triton X-100, 0.2 mM PMSF (phenylmethyl-sulfonylfluoride; Sigma, St. Louis, Mo) using a microtip. Extracts were then centrifuged at 14,000×g, for 15 minutes, to remove insoluble material. Supernatant fluids were removed and saved, and the protein concentration of each sample was determined. To prepare samples for electrophoresis, 200 μg of each extract were precipitated in 4 volumes of ice-cold methanol and resuspended to 2.5 μg per μl in 1×Laemmli SDS sample buffer and boiled for 5 minutes. Samples were electrophoresed on 6% SDS-polyacrylamide gels and transferred to nitrocellulose by electroblotting. Filters were incubated with either antibody 6E10 (1:2000), or antibody 22C11 followed by goat anti-mouse IgG (BioRad) conjugated to horseradish peroxidase (1:2000) and bands were visualized by ECL (Amersham).

Figure 22A:
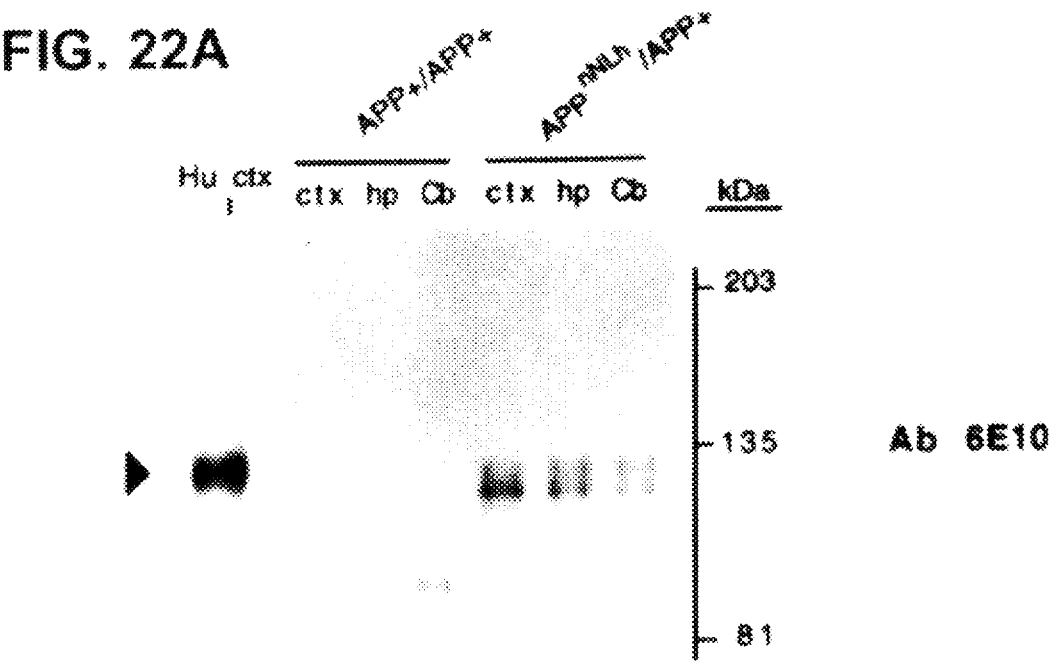
FIG. 22 is a photograph of immunoblots used for detection of 12 kD and 9 kD carboxyl-terminal derivatives of APP in targeted mouse brain.
Figure 22B:
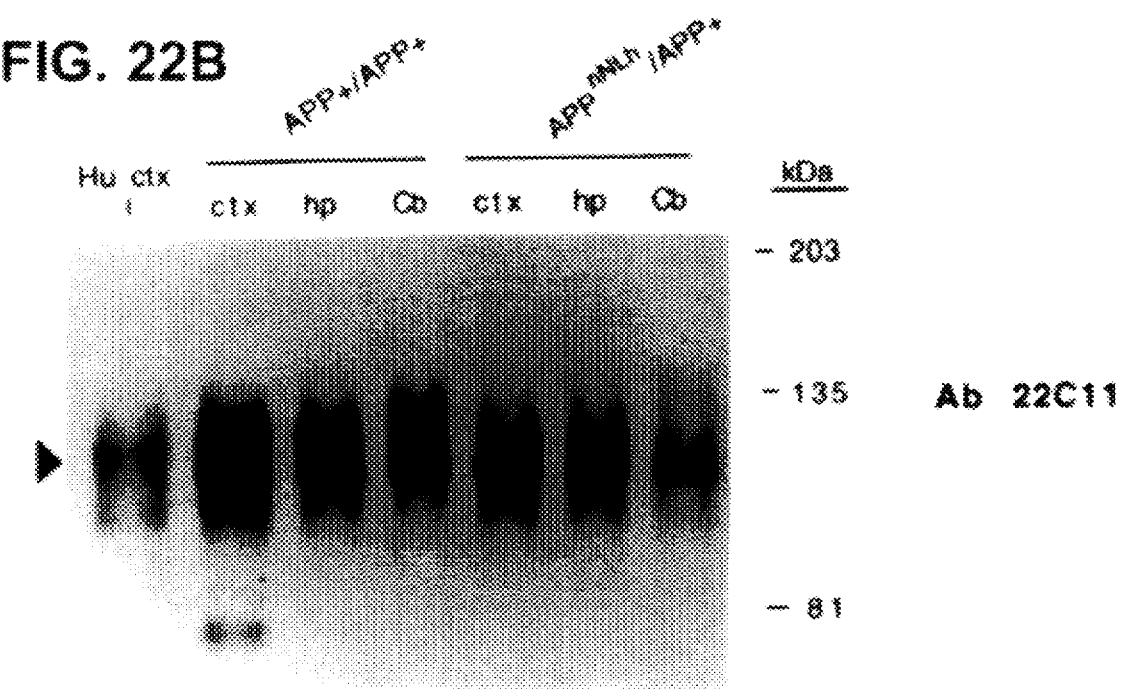

Immunoreactive species that co-migrate with the APP signal from human brain tissue were detected in extracts from neocortex (ctx), hippocampus (hp), and cerebellum (Cb) from the heterozygous APP$^{nNLh}$/APP$^+$ mouse. As expected, no signal was detected in the control APP +/APP + brain samples (FIG. 22A). Immunoblot analysis of the same samples with antibodies 22C11 (FIGS. 20 and 22B) that recognize both mouse and human APP showed no significant qualitative or quantitative differences in APP immunoreactivity between the APP+/APP+ and APP$^{nNLh}$/APP$^+$ mouse brains. These results indicate that APP with a humanized Aβ domain is being produced in the targeted mice.

Example 8 - Proteolytic Processing of Humanized APP in Mouse Brain

We predicted that the FADK670N/M671L mutations would result in enhanced expression of the human Aβ peptide. To assess the effect of the FADK670N/M671L mutations on APP processing in the mouse brain, accumulation of the 12 kD C-terminal fragment produced after cleavage at the β-secretase site was measured in control (APP+/APP+) and heterozygous (APP$^{nNLh}$/APP$^+$) mouse brain tissues. Brain homogenates were initially immunoprecipitated with antibody 97 (FIG. 20), specific for the last 30 amino acids of human and mouse APP, to concentrate all APP fragments bearing C-terminal epitopes.

Figure 23A:
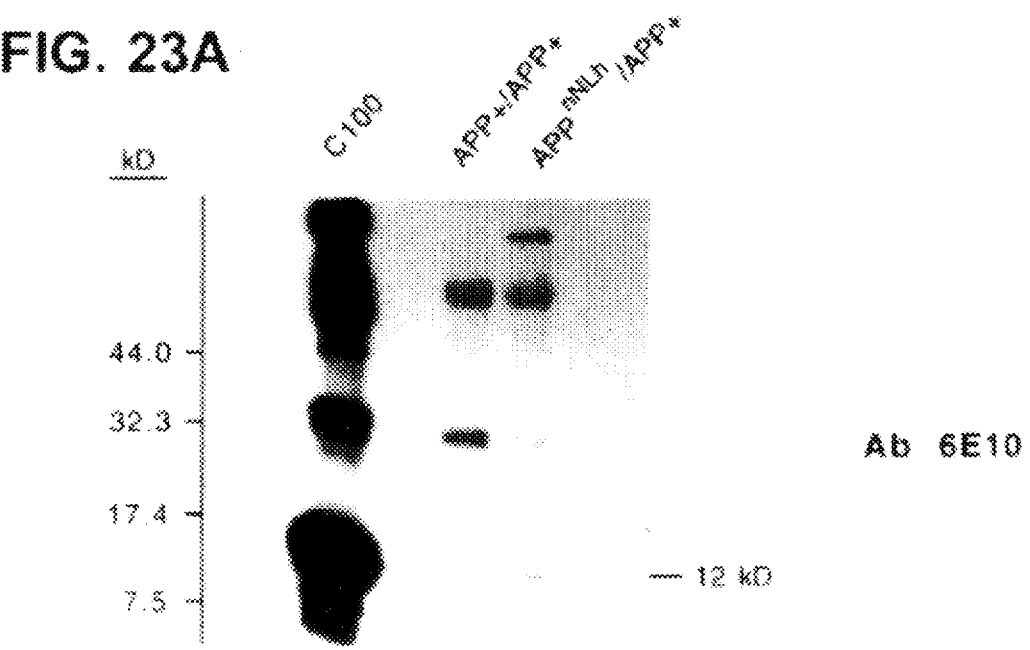
FIG. 23 is a photograph of immunoblots used for detection of 12 kD and 9 kD carboxyl-terminal derivatives of APP in targeted mouse brain.

One-half brain (~0.2 g) from each of a normal littermate control and a heterozygous targeted mouse were separately homogenized in 3 ml of buffer B (20 mM Tris-HCl (pH 7.4), 2 mM EGTA, 1 mM EDTA, 1 mM benzamidine (Sigma), 1 mM DTT, and 1 mM PMSF). Extracts were centrifuged at 100,000×g for 1 hour to fractionate the membrane and soluble fractions. Pellets, consisting of the membrane fraction, were washed in 3 ml of buffer B and re-centrifuged at 100,000×g. Resulting pellets were then sonicated in 3 ml of 1×RIPA buffer (50 mM Tris-HCl, pH 8.0, 150 mM NaCl, 1% Triton X-100, 0.1% SDS, 2 mM EDTA, 0.5% deoxycholate, 1 mM benzamidine, 0.05 mM leupeptin (Sigma), 0.02 mM pepstatin A (Sigma). The sonicated extracts were centrifuged at 100,000×g for 1 hour. Supernatant fluids were cleared prior to immunoprecipitation by incubating them for 1 hour with 2 μl of normal rabbit serum and 50 μl pansorbin (CalBiochem). After centrifugation at 3500 rpm for 10 minutes, 10 μl of rabbit antibody 97 and 30 μl of pansorbin were added to each supernatant fluid. The samples were incubated overnight at 4° C. Rabbit antibody 97, specific to the last 30 amino acids of APP conserved between human and rodent APP, was used to immunoprecipitate membrane-bound forms of APP. Immunoprecipitates were then obtained by centrifugation at 3500 rpm for 10 minutes. Pellets were resuspended in high salt 1×RIPA (1×RIPA containing 350 mM NaCl) and centrifuged at 8500 rpm for 5 minutes. After 2 additional washes of the pellet in high salt 1×RIPA, the pellets were washed in 1×TBS and resuspended in 1×Laemmli SDS sample buffer. Samples were heated in boiling water for 5 minutes and then electrophoresed on 16% Tris-tricine polyacrylamide gels (Novex) to resolve carboxyl-terminal 9 kD and 12 kD fragments of APP. The proteins in the gels were then transferred to PVDF membranes by electroblotting and analyzed using either antibody 6E10 (FIG. 23A) or 4G8 (anti-Aβ 17–24); (FIG. 23B) Wiesniewski et al., *Acta Neuropathol.* 78:22 (1989).

The 12 kD fragment in APP$^{nNLh}$/APP$^+$ brain homogenates is detected by antibody 6E10, which is specific for an epitope unique to the human Aβ peptide (epitope=human Aβ peptide residues 1–17). This confirmed that the mouse β-secretase recognized and cleaved the humanized APP. The 12 kD fragment was not detected in the control brain homogenates, because 6E10 is human-specific.

Figure 23B:
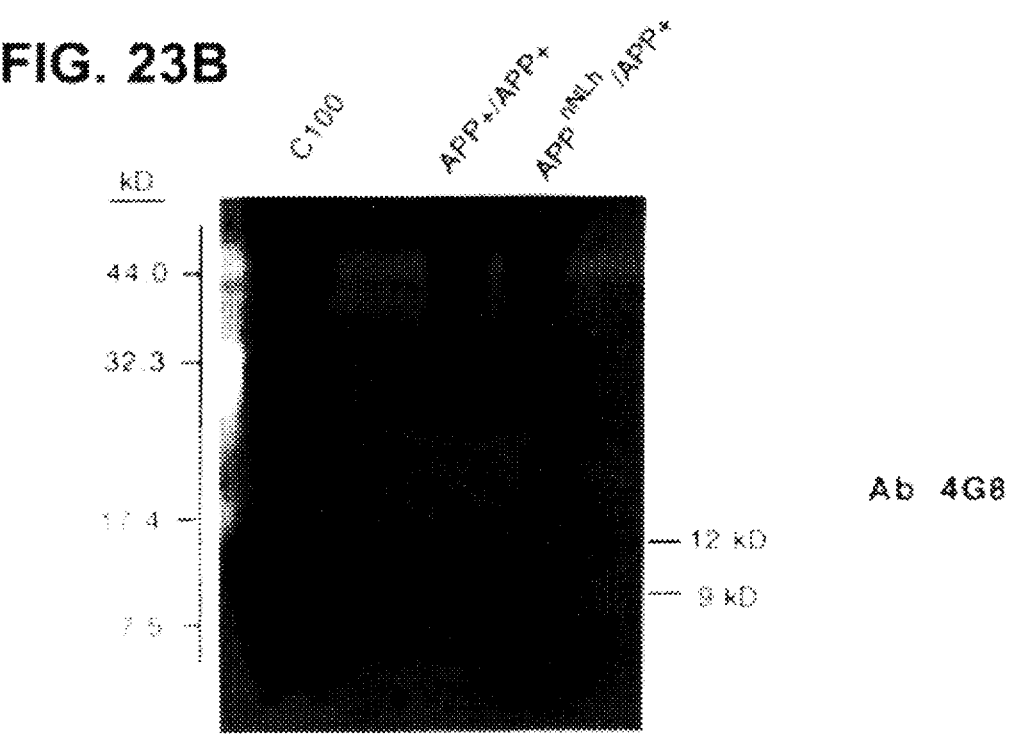

For a more direct measure on the efficiency of β-secretase cleavage between native and mutagenized APP, the immunoblots were reacted with antibody 4G8 (epitope= Aβresidues 17–24) which recognizes the 12 kD C-terminal fragment from both human and mouse APP, as well as the nonamyloidogenic 9 kD fragment produced after cleavage at the α-secretase site. A comparison of the 12 kD to 9 kD ratios is useful as a relative measure of APP processing through the amyloidogenic and nonamyloidogenic pathways. As shown in FIG. 23B, there was a significant increase in the 12 kD to 9 kD ratio in the APP$^{nNLh}$/APP$^+$ versus control brain homogenates. This indicated that the presence of the FADK670N/M671L mutations (and possibly the humanizing Aβ mutations) significantly enhanced cleavage at the β-secretase site in the mouse brain. Thus, there was an increased amount of 12 kD peptide comprising the human Aβ peptide in the brain tissues of the mice of this invention as a result of the cleavage of APP at amino acid 672 (resulting from the action of the β secretase enzyme).

In addition to confirming that the 12 kD peptide comprising the human Aβ peptide is present in brain tissues of mice homozygous for the targeted APP gene, we have determined that the 4 kD human Aβ peptide is also present in brain tissues of the mice heterozygous for the targeted APP gene. On the basis of gene dosage effects, in general, and on the basis of APP measurements performed on our APP gene-targeted mice, in particular, the mice homozygous for the targeted APP gene produce, in their brains, approximately twice as much human Aβ peptide as do the mice that are heterozygous for the targeted APP gene (see Example 9, infra).

Example 9 - Detection of Human Aβ in the APP Gene-Targeted Mouse Brain

We have examined whether enhanced cleavage at the β-secretase site was associated with an increase in human Aβ accumulation in the APP gene-targeted mouse brain. An immunoprecipitation and immunoblotting method was employed using two distinct Aβ-specific antibodies. One-half mouse brain (0.25 g) or normal human frontal cortex (70 year-old male) was homogenized in 3 ml 6M guanidine, 50 mM Tris, pH 7.5 and subsequently centrifuged at 100,000×g for 1 hour. The supernatants were dialyzed against two changes of PBS containing 1 mM benzamidine, 1 μM pepstatin A, 1 μM leupeptin, 1 μM E64, and 100 μM PMSF (all protease inhibitors from Sigma Chemical Co., St. Louis, MO) overnight at 4° C. Dialysates were immunoprecipitated with 20 μl of antibody 1153 (anti-Aβ 17–40) (Siman et al. in Research Advances in Alzheimer's Disease and Related Disorders, (Iqbal et al., eds.), Wiley and Sons, Chichester, England, pp. 675–684 (1995)). Immunoprecipitates were eluted in SDS-Tricine gel loading buffer (50 mM Tris/HCl, pH 6.8, 4% SDS, 12% glycerol, 2% β-mercaptoethanol) at 90° C., resolved by electrophoresis on 16% Tris-Tricine SDS-polyacrylamide gels and proteins were transferred to PVDF membrane (Stratagene Cloning Systems). Immunoreactive bands were detected using 1:2000 antibody 6E10, followed by goat anti-mouse IgG conjugated to horseradish peroxidase and ECL.

Figure 24A:
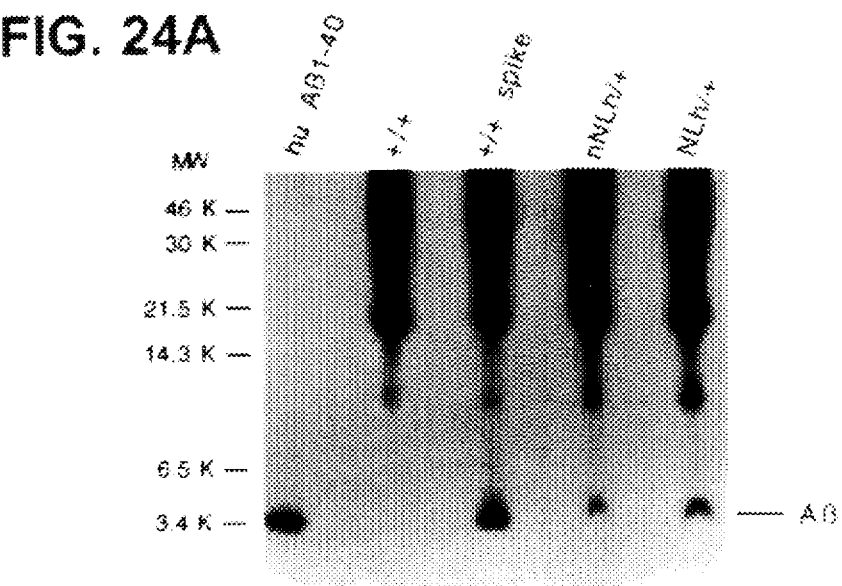
FIG. 24 is a photograph of immunoblots used for the detection of human Aβ+n human and targeted mouse brains.
Figure 24B:
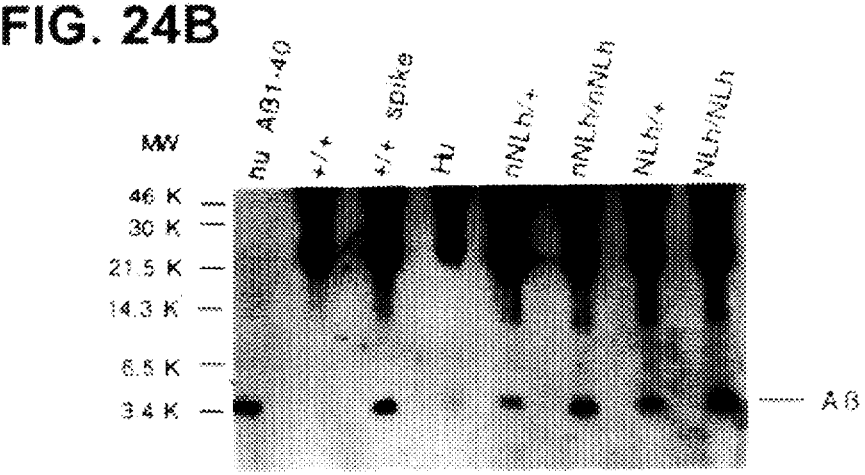
Figure 24C:
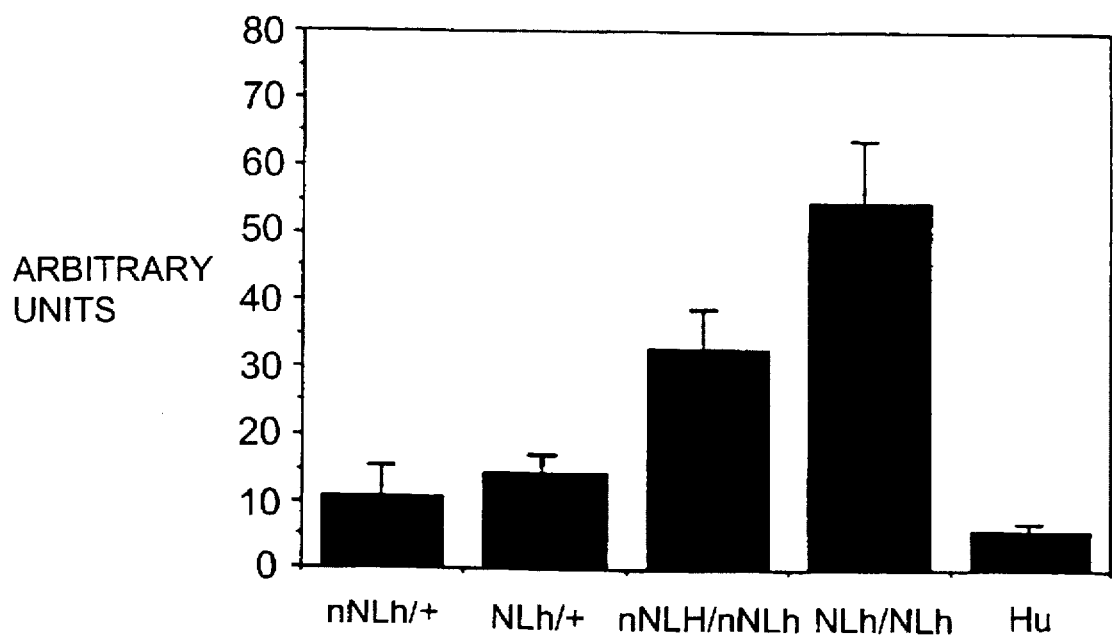

A 4kD polypeptide that co-migrated with synthetic human Aβ was detected in the brains of $APP^{nNLh}/APP^+$, $APP^{nNLh}/APP^{nNLh}$, $APP^{NLh}/APP^+$ and $APP^{NLh}/APP^{NLh}$ mice (FIGS. 24A and 24B). Due to the selectivity of Ab 6E10 for human Aβ, no immunoreactivity was found in the wild-type $APP^+/APP^+$ mouse brain. Levels of immunoreactivity in the APP gene-targeted brains also corresponded directly with gene dosage, providing further evidence on the identity of the immunoreactive species as human Aβ. The calculated levels of human Aβ in brains from the various genotypes of the APP gene-targeted mice appear in FIG. 24C. An increase of approximately 50% in human Aβ is correlated with excision of the neo selectable marker in mice that are heterozygous ($Appn^{NLh}/APP^+$ and $APP^{NLh}/APP^+$) or homozygous ($APP^{NLh}/APP^{nNLh}$ and $APP^{NLh}/APP^{NLh}$) for the mutant APP allele. This is likely to be caused by more efficient transcriptional readthrough at the targeted locus due to removal of the $neo^r$ gene cassette with its RNA processing signals. In the $APP^{NLh}/APP^{NLh}$ mouse brain, human Aβ levels were approximately 9-fold greater than those found in normal aged human brain.

Other embodiments are within the following claims.

---

We claim:

1. A gene-targeted mouse whose somatic and germ cells are homozygous for a chimeric amyloid precursor protein (APP) gene, wherein said gene comprises an endogenous mouse APP gene where at least one Swedish mutation has been introduced into said endogenous gene and where a sequence encoding human Aβ peptide replaces the corresponding region of said endogenous gene, and wherein the expression of said gene results in the formation of a detectable amount of human Aβ protein in the brain of said mouse.

2. The mouse of claim 1, wherein the Swedish mutation is selected from the group consisting of:

(a) an asparagine at amino acid position 670;

(b) a leucine at amino acid position 671; and (c) an asparagine at amino acid position 670 and a leucine at amino acid position 671.

3. The mouse of claim 1, wherein the Swedish mutation is an asparagine at amino acid position 670 and a leucine at amino acid position 671.

4. A gene-targeted mouse whose somatic and germ cells are hornozygous for a chineric amyloid precursor protein (APP) gene, wherein said gene comprises an endogenous mouse APP gene where at amino acid position 671 a sequence encoding an amino acid selected from the group consisting of tyrosine, phenylaimine and tryptophan has been introduced into said endogenous gene and where a sequence encoding human Aβ peptide replaces the corresponding region of said endogenous gene, and wherein the expression of said gene results in the formation of a detectable amount of human Aβ protein in the brain of said mouse.

5. A method of screening for the effect of compounds on the processing of amyloid precursors protein (APP) in vivo, said method comprising the steps of:

a) administering said compounds to the mouse of claim 1; and b) monitoring the effect of said compounds on APP processing in the brains of said mice.

* * * * *